United States Patent [19]
Segal

[11] Patent Number: 5,951,976
[45] Date of Patent: Sep. 14, 1999

[54] OPSONIN-ENHANCED CELLS, AND METHODS OF MODULATING AN IMMUNE RESPONSE TO AN ANTIGEN

[75] Inventor: Andrew H. Segal, Boston, Mass.

[73] Assignee: Whitenead Institute for Biomedical Research, Cambridge, Mass.

[21] Appl. No.: 08/826,259

[22] Filed: Mar. 27, 1997

Related U.S. Application Data

[60] Provisional application No. 60/014,364, Mar. 28, 1996.
[51] Int. Cl.$^6$ .............................. A61K 38/00; C12N 9/00; C12N 5/06; A01N 63/00
[52] U.S. Cl. ..................... 424/93.21; 424/93.7; 435/325; 514/12; 514/21
[58] Field of Search ................................ 424/93.21, 93.7; 435/325; 514/12, 21

[56] References Cited

U.S. PATENT DOCUMENTS 5,270,199  12/1993  Ezekowitz .

*Primary Examiner*—Paula K. Hutzell
*Assistant Examiner*—Geetha P. Bansal
*Attorney, Agent, or Firm*—Banner & Witcoff, Ltd.

[57] ABSTRACT

Disclosed are methods and compositions wherein opsonin-enhanced cells, that is, cells which have been 1) modified so as to express an opsonin from a recombinant nucleic acid, 2) modified so as to express higher levels of an endogenous opsonin, or 3) mixed with an exogenous opsonin, when administered to a subject, modulate the immune response in the recipient to a selected antigen or antigens contained in or attached to the cells.

22 Claims, No Drawings

OPSONIN-ENHANCED CELLS, AND METHODS OF MODULATING AN IMMUNE RESPONSE TO AN ANTIGEN

This application is a continuation of U.S. Provisional Application 06/014,364, filed Mar. 28, 1996.

FIELD OF THE INVENTION

The invention relates in general to the immune system, and in particular to compositions and methods of modulating an immune response to an antigen.

BACKGROUND OF THE INVENTION

Opsonins are molecules which are capable, by virtue of being contemporaneously bound or attached to both an antigen and an antigen-presenting cell (APC), of acting as a coupling agent between the antigen and the APC to allow more efficient binding, engulfment, and internalization of the antigen by the APC. This is believed to facilitate generation of an immune response, since APCs present antigen to T cells. Naturally occurring opsonins can be categorized as belonging to the innate immune system (innate opsonins), which provides first line defense against foreign antigens and an antigen recognition repertoire which does not diversify during the ontogeny of the individual, or to the acquired immune system, which provides later phase defense mechanisms based on a repertoire of antigen-specific molecules, e.g., immunoglobulins, that diversify over the ontogeny of the individual.

Families of opsonins include fragments of complement components C3 and C4, collecting, and immunoglobulins. Other opsonins include fibronectin, alpha-2-macroglobulin (a2m), and C reactive protein (CRP).

It is an object of the invention to provide compositions and methods for improved vaccines by improving the uptake of antigen by antigen presenting cells.

SUMMARY OF THE INVENTION

The invention is based, at least in part, on the discovery that opsonin-enhanced cells, that is, cells which have been 1) modified so as to express an opsonin from a recombinant nucleic acid, 2) modified so as to express higher levels of an endogenous opsonin, or 3) mixed with an exogenous opsonin can, when administered to a subject, modulate the immune response in the recipient to a selected antigen or antigens contained in or attached to the cells.

The invention therefore encompasses a method of vaccinating a mammal to a selected antigen, the method comprising administering to the mammal a vaccine composition comprising an opsonin-enhanced cell, wherein the opsonin-enhanced cell comprises the selected antigen and a nucleic acid encoding an opsonin and expresses the nucleic acid encoding the opsonin.

The invention also encompasses a method of vaccinating a mammal to a selected antigen, the method comprising administering to the mammal a vaccine composition comprising an opsonin-enhanced cell, wherein the opsonin-enhanced cell comprises the selected antigen and is admixed with an exogenous opsonin.

Preferably, the exogenous opsonin is an engineered opsonin.

The invention also encompasses a method of vaccinating a mammal to a selected antigen, the method comprising contacting an APC in vitro with an opsonin-enhanced cell comprising a selected antigen and an opsonin, for a time sufficient to permit internalization of the selected antigen by the APC, and administering the contacted APC to a mammal.

Preferably, the opsonin-enhanced cell comprises the selected antigen and a nucleic acid encoding the opsonin. It also is preferred that the opsonin is an exogenous opsonin and/or an engineered opsonin.

Preferably, in the inventive methods and compositions, the opsonin-enhanced cell is substantially unable to divide in vitro. "Substantially unable to divide in vitro" means that opsonin-enhanced cells divide at a rate that is less than about 50% with respect to corresponding cells which are not treated to prevent cell division.

It also is preferred that the vaccine composition is attenuated, and therefore is unable to cause a disease that the cells cause in their pathogenic form.

Preferably, the opsonin is one of alpha' chain of C3b or mannose binding protein.

Preferably, the antigen is a pathogenic cell, which may be a tumor cell which is malignant.

The invention also encompasses a pathogenic cell containing a selected antigen and a recombinant nucleic acid encoding an opsonin, wherein the cell expresses the encoded opsonin, wherein the opsonin is selected from the group consisting of: fibronectin, complement components C1q, C1qA chain, C1qB chain, C1qC chain, complement fragments C3b, C3bi, C3d, C3dg and C4b, mannose binding protein, conglutinin, surfactant proteins A and D, alpha-2-macroglobulin, and immunoglobulins and engineered opsonins.

Preferably, the pathogenic cell is a tumor cell which may be malignant.

It is preferred that the pathogenic cell is selected from the group consisting of: a pathogenic bacterium, a pathogenic fungus, a pathogenic virus, a cell of a pathogenic parasite. Where the invention comprises an opsonin-enhanced bacterial pathogen, it is preferred that the administered cells comprise opsonin bound to the cells.

The invention also encompasses a host cell containing and expressing a recombinant nucleic acid encoding an opsonin and a recombinant nucleic acid encoding an antigen.

Preferably, the host cell is any host cell which is able to act as a carrier for the opsonin and the antigen, and thus may be a nucleated cell or a procaryotic cell. In this aspect of the invention, the host cell need not be pathogenic, but may be any cell into which nucleic acid is introduced artificially. Such cells include but are not limited to a fibroblast, including a specialized mesenchymal cell such as a synoviocyte, a keratinocyte, an epithelial cell, an endothelial cell, a leukocyte, a tumor cell, a bacterial cell, a cell of a fungus, a cell of a parasite.

The invention also encompasses a composition comprising a cell admixed with an engineered opsonin.

Preferably, the cell is a pathogenic cell.

The invention also encompasses a composition comprising a cell admixed with an opsonin, wherein the cell is substantially unable to divide in vitro.

Preferably, the cell is a pathogenic cell.

Preferably, the composition is substantially free of culture medium. As used herein, "culture medium" refers to medium that is used in cell culture containing at least 2% animal serum, such as fetal calf serum.

The invention also encompasses a composition comprising a cell comprising a heterologous antigen, admixed with an innate opsonin, wherein the cell is substantially unable to divide in vitro.

Preferably, the composition is substantially free of culture medium.

The invention also encompasses a composition comprising a cell comprising a heterologous antigen, admixed with an exogenous engineered opsonin which is able to bind to the cell either via covalent bonding or via a receptor-ligand binding interaction, e.g., an interaction between a lectin domain of a collectin opsonin and a carbohydrate on the surface of an antigen-containing cell.

Preferably, the cell is unable to divide in a mammalian host.

The invention also encompasses a composition consisting essentially of a cell and an opsonin.

Preferably, the composition further comprises a physiologically compatible buffer, and also further comprises a cytokine, which cytokine may be expressed by the cell.

The invention also encompasses a composition consisting essentially of a cell and an opsonin, wherein the cell is substantially unable to divide in vitro.

Preferably, the composition further comprises a physiologically compatible buffer.

Compositions of the invention also may further include a cytokine, which is preferably expressed by the cell.

The invention also encompasses a vaccine composition comprising opsonin-enhanced cells and a pharmaceutically acceptable carrier.

The invention also encompasses a nucleic acid encoding a chimeric protein comprising first and second ends, wherein the chimeric protein binds via the first end to a first cell which is an APC and binds via the second end to a second cell containing a selected antigen, wherein the first end comprises an APC binding sequence (moiety or domain) from an opsonin.

Preferably, the nucleic acid also encodes a GPI-modification signal sequence.

It also is preferred that the fusion protein contains a transmembrane sequence.

The invention also encompasses an engineered opsonin, which opsonin comprises an APC binding moiety of a naturally occurring opsonin, and a heterologous moiety that binds to a cell surface.

Preferably, the heterologous moiety that binds to a cell surface comprises a lipid, which lipid may be contained in a GPI moiety. An opsonin comprising a lipid can attach to a cell via intercalation of the lipid portion into the cell plasma membrane.

As used herein, the term "vaccinating" refers to modulating an immune response to a selected antigen such that the response is more efficient, more rapid, greater in magnitude, and/or more easily induced than the response obtained from administration of corresponding cells which are identical in every respect except that they are not opsonin-enhanced cells.

The term "modulate the immune response" may refer to stimulation/activation of an immune response to a selected antigen, or it may refer to suppression, elimination, or attenuation of an immune response to a selected antigen.

A "pathogenic" cell is a cell that, without expressing the opsonin, can cause disease, e.g., a tumor cell, an autoreactive T cell, a pathogenic bacterium, a pathogenic fungus, or a cell of a pathogenic parasite. For the purposes of the invention, a pathogenic virus is a pathogenic cell. A pathogenic cell may be modified by attenuating, inactivating, or killing of a pathogenic bacterium, fungus, parasite, or virus.

"Exogenous opsonin" or "antigen" refers to an opsonin which is introduced from or produced outside the cell.

"Endogenous opsonin" or "antigen" refers to an opsonin or antigen which is expressed or present naturally in a cell.

"Heterologous opsonin" or "antigen" refers to an opsonin or antigen which is not naturally expressed in a cell.

An opsonin of an opsonin-enhanced cell may be expressed as a cytoplasmic, surface, or a secreted molecule. It is preferred, however, that the opsonin be expressed as a surface or a secreted molecule.

It is preferred that the antigen and the opsonin are nonidentical.

In another preferred embodiment, the opsonin is a recombinant opsonin which contains a transmembrane segment.

In another preferred embodiment, the opsonin is an engineered opsonin and comprises a lipid. In yet another preferred embodiment, the lipid is linked to the opsonin via a glycosylphosphatidylinositol moiety. In a further preferred embodiment, the opsonin, e.g. a collectin, can bind to the cells noncovalently. The cells can be processed, e.g. by treatment with a glycosyltransferase or a glycosidase, to facilitate such noncovalent binding.

If the opsonin can be inactivated by a molecule comprised by the cell, as, for example, C3b can be inactivated by CD46, an inhibitor of the inactivator, e.g. an antibody, can be included in the composition.

Preferably, the opsonin-enhanced cells are mixed with a cytokine, such as GM-CSF, IL12, IL10, IL4, or a chemokine, or are transformed with a gene encoding a cytokine.

The term "opsonin" as used herein refers to naturally occurring and non-naturally occurring molecules which are capable, by virtue of being contemporaneously bound or attached to both an antigen-containing cell and an antigen-presenting cell (APC), of acting as a link or coupling agent (an adapter) between the antigen and the APC to allow more efficient binding, engulfment, and internalization of the antigen-containing cell by the AIRC. To fall within the definition of an opsonin useful according to the invention, non-naturally occurring opsonins will bind to APCs via receptors that can bind naturally occurring opsonins.

The term "opsonin" as used herein can also refer to molecules which can be processed such that at least one product of the processing step or steps is capable of, by virtue of being contemporaneously bound or attached to both an antigen-containing cell and an APC, acting as a link or coupling agent to allow more efficient binding, engulfment, and internalization of other antigen-containing cells by the APC. An opsonin can also be any polypeptide chain of a multichain opsonin.

Examples of opsonins which are useful in the methods and compositions of the invention include the following: fibronectin, complement components such as C1q (including any of its component polypeptide chains A, B and C), complement fragments such as C3b and C4b, mannose binding protein, conglutinin, surfactant proteins A and D, C-reactive protein (CRP), alpha-2-macroglobulin, and immunoglobulins, for example, the Fc portion of an immunoglobulin.

"Innate opsonins" are opsonins of the innate immune system and are known in the art as secreted polypeptide molecules of the innate immune system and are believed to bind contemporaneously to an antigen and to the surface of an APC. They can thus act as "bridges", and are thought, by virtue of this property, to promote internalization of antigens by APCs. The mode in which opsonins bind to antigens varies among opsonins, and can be covalent or noncovalent. In general, the antigen-binding moieties of innate opsonins differ from the antigen-binding moieties of immunoglobulins in that the former are relatively invariant among members of the same species, and do not undergo diversification during the ontogeny of an individual.

A molecule containing a naturally occurring APC-binding moiety shall be considered an opsonin if it contains a moiety through which it can be stably bound or attached to a cell such that the APC-binding moiety is located in the extracellular space, whether or not the opsonin molecule contains its natural antigen-binding domain.

"Engineered opsonins", as described herein, include molecules in which a cell membrane binding moiety is substituted for the natural antigen-binding domain of an opsonin or where a cell membrane binding moiety is linked to the opsonin without modification or removal of the natural antigen-binding domain of the opsonin.

A "cell membrane binding moiety" of an engineered opsonin, i.e., a moiety through which a molecule can be stably bound to a cell, includes but is not limited to crosslinking moieties, transmembrane sequences, and lipid moieties. In a preferred embodiment, a lipid moiety is linked to the engineered opsonin via a glycosylphosphatidylinositol (GPI) moiety. In another preferred embodiment of the invention, the cell membrane binding moiety is linked to the opsonin or the antigen-binding domain-truncated opsonin at the antigen-binding end of the opsonin. In another preferred embodiment, the engineered opsonin comprises an idiotypic portion of an immunoglobulin which can bind to an APC.

It is preferred that the opsonins bind to receptors that trigger phagocytosis and that are non-clonotypic and thus do not vary from cell to cell as, for example, clonotypic receptors do. Non-clonotypic receptors are present on cells which play a role in innate immunity, and include, e.g., non-idiotypic receptors. Examples of such receptors include CR1, CR2, CR3, CR4, and C1q receptor, receptors containing a component of the C1q receptor, collectin receptors, receptors for a2m, receptors for CRP, and Fc receptors for immunoglobulins.

The term "antigen" as used herein refers to a molecule which can initiate a humoral and/or cellular immune response in a recipient of the antigen. Antigens can be any type of biologic molecule including, for example, simple intermediary metabolites, sugars, lipids, and hormones as well as macromolecules such as complex carbohydrates, phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, and other miscellaneous antigens.

The opsonin-enhanced cells of the invention, can be used, for example, to modulate an immune response in a human to an antigen or antigens contained in the cells. The cells are either administered to a mammal, preferably a human, and are taken up (i.e., ingested or phagocytosed) by antigen presenting cells. Alternatively, the cells are contacted with antigen presenting cells in vitro under conditions which allow phagocytosis.

As used herein, "antigen presenting cell" or "APC" refers to cells that ingest and present antigen to T cells. These cells include phagocytic leukocytes, macrophages, and dendritic cells, B lymphocytes, and endothelial cells.

The vaccine compositions of the invention can be used, for example, to modulate an immune response in a mammal such as a human.

The cells of the invention can also be administered in combination with non-opsonin molecules known to be capable of modulating immune responses, such as cytokines and cell-surface molecules.

The invention also pertains to transgenic animals, the cells of which have been caused to express, in vivo, an opsonin or opsonins.

DESCRIPTION

The invention is based, at least in part, on the discovery that cells can be caused to express an opsonin, or caused to express higher levels of an opsonin. It has been observed that cells which have been caused to express an opsonin, or which are admixed with an opsonin, (herein referred to as "opsonin-enhanced cells") can, when administered to a subject, modulate the immune response in the recipient to an antigen or antigens contained in or attached to the cells.

Opsonins Useful According to the Invention

As defined hereinabove, "opsonin" refers to naturally occurring and non-naturally occurring molecules which bind to both antigens and antigen presenting cells (APCs), such as, for example, phagocytic leukocytes (including monocytes and macrophages), dendritic cells (for example, Langerhans cells of the skin), B lymphocytes and, in humans, endothelial cells, or molecules which can be processed such that at least one product of the processing step or steps can bind to both antigens and antigen presenting cells (APCs), such as, for example, phagocytic leukocytes, dendritic cells, B lymphocytes, and, in humans, endothelial cells.

Without being bound to any one mechanism of action, it is believed that opsonin-enhanced cells provide a beneficial effect according to the invention because the opsonin portion acts as a link or coupling agent between the antigen and the APC to allow more efficient binding, engulfment, and internalization of the antigen. In addition, the opsonin itself can be internalized with the antigen. "Internalization" refers to the cellular uptake of a molecule such that it is brought into the cytoplasm or a compartment within the cytoplasm of the cell. Phagocytosis is a process by which a molecule is internalized by a cell.

Preferred opsonins are non-rodent opsonins, e.g., primate, e.g., human, opsonins. Opsonins useful according to the invention bind to receptors on APCs (e.g., phagocytic leukocytes, e.g., macrophages and other cells of the phagocytic system) such as receptors on cells which play a role in innate immunity, as described herein.

Some sets of opsonins can be regarded as structurally and functionally similar. For example, one family comprises fragments of complement components C3 and C4. These two components are highly structurally homologous, and each possesses an intramolecular thiolester bond that is broken when a peptide (C3a or C4a respectively) is proteolytically cleaved from the native molecule. Disruption of the thiolester makes available a chemical structure that can form an ester linkage with an antigen. The moiety of C3 on which this ester bond resides, i.e. the non-C3a moiety, is designated C3b, and C4b is the analogous product of C4 cleavage. C3b can be further proteolysed by proteins such as factor I to yield fragments such as C3bi and C3d, which also remain linked to the antigen via the ester bond.

There are four structurally unique proteins that are known to function as high affinity receptors for biologically active, membrane-bound fragments of C3 and/or C4. CR1 is the major receptor for the C3b fragment of C3 and C4b fragment of C4. It is expressed on monocytes and monocyte-derived APCs, among other cell types. CR2 is the major receptor for the fragment of C3 known as C3d, and is expressed on, e.g., mature B lymphocytes, but not on cells of monocytic lineage. The major role of CR2 on B lymphocytes is believed to be direct costimulation of B cells in concert with their cognate antigens.

CR3 is expressed primarily by neutrophils and monocytes and is also expressed on FDC, Kupffer cells, and NK cells. CR3 is a C3 fragment receptor with a primary specificity for C3bi. CR3 has been proposed as an important organizer of cytoskeletal events necessary for adhesive interactions and membrane reorganization during processes such as phagocytosis.

CR4 is a member of the beta2 integrin family, and its alpha chain is structurally similar to the alpha chain of CR3 and LFA-1. Its primary physiologic ligands are believed to be C3d and C3d,g;, however, its biologic activities are less well understood than CR3.

Another example of a family of innate opsonins is the collectins, a group of collagenous C-type lectins that comprises complement component C1q, mannose binding protein, surfactant proteins A and D, and conglutinin. Each molecule comprises a lectin domain that can bind to an antigen, and a collagenous domain that can bind to receptors on phagocytic mononuclear cells, including receptors that are wholly or partially identical to the C1q receptor (Nepomuceno et al, Immunity 6:119–29; Tenner et al, Immunity 3:485–93; Guan et al, J Immunol 152:4005–16; Geertsma et al, Am J Physiol 267:L578–84; Miyaniura et al, Biochem J 300:237–42; Malhotra et al, J Exp Med 172:955–9; Malhotra et al, Biochem J 293:15–19). Most known collectins comprise multiple polypeptide chains, in some cases homomeric and in others heteromeric, that are assembled post-translationally, in part by covalent cross-linkage of hydroxyproline and hydroxylysine residues. Collectins are demonstrated to be opsonins in, for example, Pikaar et al, J Infect Dis 172:481–9; Alvarez-Dominguez et al, Infection & Immunity 61:3664–72; Kuhlman et al, J Exp Med 169:1733–45; and Geertsma et al, op cit.

Among the other innate opsonins useful according to the invention are C-reactive protein (CRP), alpha-2 macroglobulin, and fibronectin. CRP, a member of the pentraxin family of molecules, binds to receptors on cells of monocytic lineage and has been shown to be an opsonin (Tebo and Mortenson, J Immunol 144:231–8; Holzer et al, J Immunol 133:1424–30). Alpha-2 macroglobulin, like C3 and C4, comprises an internal thiolester bond that can be disrupted when the molecule is proteolysed. Such disruption allows covalent binding of the molecule to an antigen, and binding of alpha-2 macroglobulin to an APC can promote uptake of the conjugate. Fibronectin binds to the alpha 5 beta 1 integrin and can also bind to various antigens, allowing it to function as an opsonin (Cosio, J Lab Clin Med 103:613–9; Czop and Austen, J Immunol 129:2678–81).

Immunoglobulins (antibodies) can function as opsonins by binding antigens via their variable regions and APCs via their constant regions. Typically, an immunoglobulin comprises two heavy chains which are covalently bound to each other and each of which is bound to one light chain. These heterotetramers can further assemble into higher-order structures, such as the pentamers of IgM. Both heavy and light chain variable regions can contribute to the structure of the antigen binding site, whereas the APC binding site is located on the heavy chain constant region. Recombinant single-chain antibodies have also been described. APC receptors for immunoglobulins include Fc alpha, Fc gamma, Fc epsilon, and Fc mu receptors for IgA, IgG, IgE, and IgM, respectively.

Opsonins that are naturally expressed by multicellular eukaryotic organisms are secreted. The latter characteristic distinguishes opsonins from adhesion molecules. A non-naturally occurring molecule containing a naturally occurring APC-binding moiety shall be considered an opsonin if it contains a moiety through which it can be stably bound or attached to a cell such that the APC-binding moiety is located in the extracellular space, whether or not the molecule contains an antigen-binding moiety of a naturally occurring antigen. Moieties through which molecules can be stably bound to a cell include crosslinking moieties, transmembrane sequences, and lipid moieties. The preparation of proteins containing these sequences or moieties is well-known to one of skill in the art.

An "APC binding moiety of an opsonin" is a sequence or domain of an opsonin which when included in a chimeric molecule permits binding of the chimeric molecule to a receptor that is physiologically expressed on an APC with an affinity at least in the nanomolar range.

There are a number of examples of opsonin fragments that comprise APC binding moieties. Such a fragment may be any length so long as it retains an APC binding function; for example, it may be about 40 amino acids, 100 amino acids, 150 amino acids, 500 amino acids, 800 amino acids, or even as long as 3000 amino acids. For example, Las Holtet et al, 1994, FEBS Lett 344:242 describe a carboxy-terminal fragment of human a2m (val1299-ala1451) that binds with high affinity to the a2m receptor. Fragments comprising amino acids 1314–1451 of human a2m and the corresponding domain of rat a2m also bind to a2m receptors, albeit with 1–2% of the affinities of native a2m (Van Leuven et al, 1986, J Biol Chem 261:11369; Enghild et al, 1989, Biochemistry 28:1406; Salvesen et al, 1992, FEBS Lett 313:198; Sottrup-Jensen et al, 1986, FEBS Lett 205:20).

Becherer and Lambris, 1988, J Biol Chem 263:14586 describe fragments of C3b that bind to CR1, e.g., C3c, fragments of C3 generated by elastase treatment and comprising the N-terminal of the alpha' chain of C3b, and a synthetic peptide comprising the 42 N-terminal amino acids of the C3b alpha' chain. A binding sequence in C3 for CR3 has also been described (Wright et al, 1987, PNAS 84:4235).

"Collagen stalks" of C1q, which are N-terminal fragments obtained by pepsin digestion, bind to the C1q receptor (Reid, 1981, Methods Enzymol 80:16; Malhotra et al, 1993, Biochem J 293:15). Malhotra et al, ibid., also provide evidence that an APC binding moiety of conglutinin is comprised by its 55 N-terminal amino acids. Ezekowitz (U.S. Pat. No. 5,270,199) offers a putative APC binding site in human mannose binding protein consisting of nucleotides 370–438 of FIG. 2 in the '199 Patent. In addition, by homology with conglutinin, exon 1 disclosed in the '199 Patent may comprise an APC binding moiety.

An APC binding moiety of IgG comprises the CH2 domain and the lower hinge region, including residues 234–237, as described by Canfield and Morrison, 1991, J Exp Med 173:1483–91; Lund et al, 1991, J Immunol 147:2657–62; and Sarmay et al, 1992, Mol Immunol, 29:633–9.

Examples of opsonins which can be used in the compositions and methods of the invention include fibronectin (e.g., Genbank accessions X02761, K00799, K02273, X82402, X00307, X00739), CRP (e.g., Genbank accessions X17496, M11880, M11881, M11882), complement components such as C1q (e.g., Genbank accessions X66295, M22531, X03084, X58861, and Swiss-Prot accessions P02747, P02745), complement fragments such as C3b and C3d (e.g., Genbank accessions K02782, K02765), mannose binding protein (e.g., Genbank accessions S42292, S42294, X15422), conglutinin (e.g., Genbank accession X71774), alpha-2-macroglobulin (e.g., Genbank accessions M93264, M11313), and surfactant proteins A (e.g., Genbank accessions M68519, S48768) and D (e.g., Genbank accessions L40156, X65018, S38981), immunoglobulins, and their homologues among species.

TABLE 1

Exemplary Opsonin, APC binding moiety/APC receptor pairs useful according to the invention.

| Opsonin | Exemplary APC Binding Moiety | Receptor |
|---|---|---|
| α-2 macro-globulin | Val(1299)-Ala(1451) of human α-2m | α-2m receptor |
| C3b | 42 N-terminal amino acids of the α' chain of human C3b | CR1 |
| C3bi | C3bi | CR2, CR3 |
| C3d | C3d | CR2, CR4 |
| C1q | Collagen stalks (Reid, 1981, Methods Enzymol. 80:16) | Collectin receptor (Nepomuceno et al., 1997, Immunity 6:119) |
| Conglutinin | 55 N-terminal amino acids of bovine conglutinin | Collectin receptor |
| MBP | 1. Polypeptide encoded by nt 370–438 of FGF. 2, U.S. Pat. No. 5,270,199<br>2. Polypeptide encoded by Exon. I of FIG. 2, U.S. Pat. No. 5,270,199 | Collectin receptor |
| CRP | CRP | CRP receptor |
| Fibronectin | Fibronectin | α5β1 integrin |
| IgG | CH2 domain plus lower hinge including amino acids 234–237, as described by Lund et al., 1991, J. Immunol. 147:2657 | FcγRI |
| Surfactant Protein A | Surfactant Protein A | Collectin receptor |
| Surfactant Protein D | Surfactant Protein D | |

Determination of Opsonicity According to the Invention

A given naturally occurring opsonin is considered useful according to the invention if it is determined to possess opsonicity according to one or more of the following assays, and if it is a secreted molecule.

Assay 1

In one assay of opsonicity, as described by O'Rear and Ross in Current Protocols in Immunology, 1994, John Wiley & Sons, pp. 13.4.5–9, SRBC bound via a physiologically occurring linkage to the candidate opsonin molecule are obtained. APCs from the species to which the candidate opsonin is native are suspended at $4 \times 10^6$/ml in ice-cold HBSS with 1% (w/v) Cohn fraction of BSA. If the candidate opsonin is a fragment of C3, the APCs are freshly drawn, uncultivated peripheral blood monocytes. SRBC linked to the candidate opsonin or control SRBC (identical to the former but not linked to the candidate opsonin) are suspended in the same solution at $2 \times 10^8$/ml. 100 ul of SRBC suspension and 100 ul of APC suspension are mixed in a 10×75 mm plastic tube. The tube is rotated at 40 rpm at 37° C. for 2–20 min. A small drop of the suspension is placed on a slide, covered with a coverslip, and allowed to stand for 5–10 min. Excess fluid can be removed by pressure on the coverslip, and the coverslip can be sealed to the slide, e.g. with clear nail polish. The slide is examined microscopically, and the percentage of APCs visibly adherent to 4 or more SRBCs is determined. If said percentage is 50% or greater when there are up to $4 \times 10^4$ candidate opsonin molecules/SRBC, the candidate opsonin can be an opsonin.

Assay 2 (For Protease-activated Candidate Opsonin)

Candidate opsonin or radiolabeled Candidate opsonin is treated with a 1.5–3 fold molar excess of protease (0.05 M triethanolamine-0.1 M NaCl, pH 8.0, room temperature overnight). In this assay, the protease can serve as the antigen or an excess of another antigen can be added. Prior to binding studies, the candidate opsonin-antigen complex is dialyzed against HBSS (4° C.).

Candidate opsonin-antigen complex binding to monocytes is measured by incubating labeled ligand at a concentration up to 1.0 M with (1.5–4.0) $\times 10^6$ monocyltes in 200 μl volume on ice. Nonspecific binding of radiolabeled ligands is determined in the presence of a 100-fold molar excess labeled candidate opsonin-antigen complex. The unbound ligand is separated from the cells and cell-bound ligand by rapid vacuum filtration on glass fiber filters. Studies are performed on ice to avoid potential complications due to endocytosis. Binding constants and the number of sites per cell are determined by analysis and by nonlinear curve fit. If candidate opsonin-antigen complex affinity for a monocyte binding site is in at least the nanomolar range, the candidate opsonin is an opsonin. Assay 3

Part I

To directly evaluate whether candidate opsonin is bound to the surface of *P. carinii*, immunoelectron microscopy is performed. *P. carinii* are isolated from bronchoaveolar lavage (BAL) of moribund infected rats using TBS with 1 mM calcium to preserve surface-bound candidate opsonin. Isolated organisms are fixed in periodate-lysine-parafoirnaldehyde buffer and embedded in Lowacryl mounting medium (Ted Pella, Inc., Redding, Calif.). Ultrathin sections are obtained, blocked with normal goat serum (2%) for 1 h, and incubated with either rabbit anti-candidate opsonin or nonimmune rabbit IgG (25 μg/ml) overnight. After washing, the sections are subsequently incubated with goat and rabbit IgG conjugated to 15 nM colloidal gold (Amersham Corp., Arlington Heights, Ill.). The sections are washed again and examined on a transmission electron microscope (model 6400:JEOL USA, Inc., Peabody, Mass.).

Part II

The attachment of *P. carinii* to cultured alveolar macrophages in the presence or absence of antibody to SP-D or with the addition of purified SP-D is quantified as follows. Adherence of *P. carinii* to alveolar macrophages is assayed by $^{51}$Cr-labeling the organisms. *P. carinii* are isolated from infected rats with TBS containing 1 mM calcium to prevent loss of surface-bound candidate opsonin. The organisms are radiolabeled by incubation for 8 h at 37° C. in 2 ml of DME containing 20% FCS and 200 μCi of $^{51}$Cr-sodium chromate (New England Nuclear). Normal alveolar macrophages are lavaged from healthy rats and plated in tissue culture plates ($1 \times 10^5$) cells/well) which are been precoated with normal rat IgG (100 μg/ml ×60 min) in order to ensure firm adherence of the macrophages. After 1 h, the macrophages are gently washed with HBSS to remove nonadherent cells. >95% of macrophages are adherent after this wash. $^{51}$Cr-*P. carinii* ($1 \times 10^6$) containing surface-associated candidate opsonin are added to the macrophages and incubated at 37° C. for an additional hour. Subsequently, nonadherent *P. carinii* are removed by washing. The macrophage monolayers containing adherent *P. carinii* are solubilized in 1 N NaOH and quantified. Adherence of *P. carinii* is defined as: percentage of adherence=(A/A+B)×100, where A=$^{51}$Cr-*P. carinii* associated with the monolayer, and B=unattached $^{51}$Cr-*P. carinii*. To assess the effect of candidate opsonin on the attachment of *P. carinii* to alveolar macrophage lung cells in culture, *P. carinii* adherence assays are conducted in the presence or absence of a polyclonal rabbit antibody generated against the candidate opsonin (100 µg/ml).

If candidate opsonin binding to *P. carinii* is apparent in Part I and if, in Part II, % adherence is diminished in the presence of anti-candidate opsonin with statistical significance of P<0.05, the candidate opsonin is an opsonin.

Assay 4

Association of bacteria with adherent monocytes is measured as follows. Endotoxin level in the modified PBS and in all buffers used is below 50 pg/ml as determined by the Limulus assay. 5×10$^3$ monocytes in modified PBS are allowed to adhere to the wells of a Terasaki plate for 2 h at 37° C. After nonadherent cells are removed by three washes with PBS, 5×10$^4$ FITC-labeled bacteria in 0.5 ml buffer with or without 10–50 micrograms/ml of candidate opsonin are added. A bacteria-to-monocyte ratio of 10:1 to 50:1 is used. After 30 min of incubation at 37° C. in the dark, the nonadherent bacteria are removed by five washes with warm PBS. Assays are performed in quadruplicate; in each well, the number of bacteria associated with ≧100 monocytes is counted under a flourescence microscope using×400 magnification. Results are expressed as the number of bacteria associated with 100 monocytes. If this number with candidate opsonin can be at least twice that without candidate opsonin, the candidate opsonin is an opsonin.

Assay 5

Part I

About 1×10$^7$ to 6×10$^7$ bacteria per ml are incubated (20 min, 0° C.) with 10 mcg/ml of $^{125}$I-candidate opsonin in a total volume of 0.7 ml. of PBS aliquots, 100 µl, of the reaction mixtures are layered over 150 µl of an oil cushion (60% dibutyl phthalate, 40% dioctyl phthalate [Eastman Kodak Co., Rochester, N.Y.]), and the mixtures are centrifuged (10,000×g, 60 s, 4° C.). The tip of the tube, containing the cell pellet, is cut with a Mozart razor blade, and the radioactivity is counted.

Part II

APCs are plated in 96-well tissue culture plates (Costar, Cambridge, Mass.) at 2×10$^5$ cells per ml the evening before use. 2×10$^6$ bacteria per well (0.1 ml per well) are added to the culture plates with or without 100 mcg/ml of candidate opsonin. The plates are then centrifuged at 1,000×g for 7 min. After 15 min at 37° C. to allow the uptake of bacteria, free bacteria are removed by several washes with cold PBS. They are then incubated (45 min, 37° C.) in RPMI 1640 plus an amount of antibiotic that, when present in the culture for 45 min, kills all extracellular bacteria. The end of this incubation period is considered time zero. Monolayers are washed three times with Hanks' balanced saline solution, and the same volume of RPMI 1640 (R0) is added. The cells are lysed by using several cycles of freezing and thawing. The number (CFU) of viable bacteria per well is determined by quantitative plate counts on blood agar plates (Columbia blood agar; Becton Dickinson, San Jose, Calif.) after 24 h of incubation. Each result is given as the mean of three determinations.

If, in Part I, candidate opsonin-treated bacterial pellet has >75 KCPM and this incorporation can be inhibited by unlabeled candidate opsonin, and if in Part II the CFU with candidate opsonin is greater than without (P<0.05), the candidate opsonini can be an opsonin.

Assay 6

200 µl of GHBSS (Hanks Balanced Salt Solution) +0.1% of gelatin containing 10 m mol CaCl$_2$) containing 10$^7$ bacteria is prepared. The bacteria are then incubated at 4° C. with 20–100 µg/ml of candidate opsonin. Binding assays are done in the presence or absence of a competitive inhibitor. After incubation for 30 minutes, the bacteria are washed five times in a GHBSS+10 mmol CaCl$_2$ at room temperature in a microfuge at 1,300 g for 3 minutes. Thereafter, a 1:1,000 dilution of rabbit anti-candidate opsonin antiserum is incubated with the bacteria for 1 h in PBS+5% FCS and 10 mmol CaCl$_2$ and then the bacteria are washed three times in GHBSS+10 mmol CaCl$_2$ plus 0.05% Tween 20. Binding of anti-serum to bacteria is detected by a 1:1,000 dilution of goat anti-rabbit IgG conjugated to rhodaimne (Fisher Pharmaceuticals, Orangeburg, N.Y.). After incubation, the bacteria are washed five times in GHBSS+10 mmol CaCl$_2$ plus 0.05% Tween 20, smeared onto glass slides and allowed to air dry. Thereafter bacteria are fixed with 100% ice cold methanol for 5 minutes. Negative controls included the absence of candidate opsonin and no first step antibody. Numerous fields of triplicate assays are examined by fluorescence microscopy.

Part II Association of Radiolabeled Bacteria with Cells.

10$^7$ radiolabeled bacteria are resuspended in 200 µl of GHBSS+10 mmol CaCl$_2$ and are incubated with or without candidate opsonin ranging from 2 µg/ml to 40 µg/ml at 4° C. for 30 min. The bacteria are then washed three times in GHBSS+10 mmol CaCl$_2$ for 3 min at room temperature in a microfuge at 1,300 g, resuspended in 50 µl of GHBSS and added to a 1-ml suspension containing on the order of 10$^6$ APCs (GHBSS). The bacteria and APCs are gently rocked at 37° C. for 20 min and thereafter the unattached bacteria are removed by five washes using differential centrifugation at 82 g in a microfuge. Before the last wash, an aliquot from each sample is plated on a Labtek slide and cells are adhered for 10 min, fixed in methanol, stained with Giemsa, and scored by light microscopy. To score the cells plated on the Labtek slides, at least 400 cells are counted. The phagocytic index represented the number of attached or ingested particles per 100 PMNs. The pellet from above containing cells and radiolabeled bacteria is then lysed in 100 µl PBS+0.5% Triton X-100 and the radioactivity is measured in a scintillation counter. If, in Part I, specific binding of candidate opsonin to bacteria is evident, and in Part II the specific uptake of bacteria, in cpm, is more than three times greater with candidate opsonin than without, the candidate opsonin can be an opsonin.

Assay 7

Part I

To investigate binding to *L donovani promastigotes* cultures are seeded at 5×10$^5$ parasites ml$^{-1}$. At regular time points up to 9 days, a fraction of parasites are counted, washed, and resuspended in 1% BSA, 0.5 mM Ca$^{2+}$. 0.05% NaN$_3$, Tris-buffered saline (TBS), (10 mM Tris-HCl, 0.15 M NaCl, pH 8.0) (diluent) to 2×10$^5$ ml$^{-1}$. Fifty microliters of this suspension are then added to 200-µl microfuge tubes containing 70 µl 5 µg/ml radiolabled C-reactive protein (CRP) (0.12 µCi/µg) in diluent without EDTA, which had been layered over 150 µl of a dinonyl phthalate/dibutyl phthalate (40:60 v/v) oil mixture. Parasites are incubated for 1 h and centrifuged through the oil layer, the cell pellet Is cut off, and associated CRP is detected by gamma counting. Each assay is performed in triplicate. The concentration dependency of CRP binding to promastigotes is also measured as above, using an activity of 0.045 µCi/µg and a twofold dilution series from 60 to 0.015 µg/ml CRP.

Part II

APCs are plated out at 1×10⁶ cells/well on glass coverslips in a 24-well tissue culture plate. Cells are incubated in RPMI 1640 (Life Technologies) supplemented with 10% PCS, 1 mM glutamine, 200 U/ml penicillin and 200 μg/ml streptomycin in a humidified incubator at 37° C. After 24 h, nonadherent cells are removed and remaining cells are used after 6 days. Promastigotes are incubated with or without CRP at 30 μg/ml in RPMI 1640 for 1 h and then washed three times before adding to the APC cultures at 10⁶/well. Promastigotes are allowed to infect APCs for 1 h, then cells are washed, fixed with methanol, and Geimsa stained (BDH, Poole, Dorset, U.K.) before counting. The percentage of APCs infected and the number of parasites/100 macrophages is determined from quadruplicate cultures.

If in Part I the affinity of candidate opsonin for parasites is at least in the nanomolar range and in Part II the number of parasites taken up/100 APCs is, with candidate opsonin, at least twice that without candidate opsonin, the candidate opsonin can be an opsonin.

Assay 8

Part I

Portions (0.5 ml) of [$^{35}$S] methionine-labeled culture medium containing 5 percent fetal calf serum and the candidate opsonin are incubated for 30 minutes at room temperature with 0.1 ml or 0.2 ml of a 10 percent suspension of a microorganism). The microorganisms tested may include, for example, *Salmonella typhimurium, Bacillis subtilis, Staphylococcus aureus, Escherichia coli*, and *Saccharomnyces cerevisiae*. Bound proteins are released by boiling in buffer containing 2 percent SDS and 0.1 M dithiothreitol and are analyzed on a 5 percent SDS gel.

Part II

Fixed bacteria (0.1 ml; 10 percent by volume; 10$^{10}$ organisms per milliletter), labeled with [$^3$H]thymidine, are incubated with 0.1 ml of serum with or without depletion of the candidate opsonin. After being washed with PBS, the bacteria are incubated with on the order of 1×10⁷ APCs in a final volume of 0.9 ml PBS containing divalent cations. At intervals 0.2 ml is removed to ice-cold PBS with N-ethyimaleimide (2mM) to block further endocytosis, and the cells are washed (at about 100 g for 10 seconds)

If in Part I a band corresponding to the candidate opsonin is apparent, and if in Part II the CPM after 6–10 min of incubation is at least three times greater for undepleted samples with serum than with depleted serum, the candidate opsonin can be an opsonin.

In lieu of results form Parts I of assays 3, 5, 6, 7, 8, a candidate opsonin that satisfies Part II of an assay can be an opsonin if it can bind to the antigen of the assay with an affinity in at least the nanomolar range.

Assay 9

SRBC coated with at least 1.2×10⁴ molecules/cell of a fragment of C3 are prepared as described by O'Rear and Ross in Current Protocols in Immunology, 1994, John Wiley & Sons, pp. 13.4.5–9. 250 ul of monocytes at 2×10⁵ cells/ml of RPMI with 10% fetal calf serum are added to each well of an 8-well glass tissue culture plate and incubated at 37° C., 5% CO$_2$ for 3h. The monocytes are washed twice with HBSS, and 50 ul of the SRBC at 1.5×10⁸/ml of DVBS$^{2+}$ are added to each well. The plate is centrifuged at 50g for 5 min and then incubated at 37° C., 5% CO$_2$ for 3h. The walls are washed twice with HBSS, fixed with 0.5% glutaraldehyde, and stained with Giemsa stain. If >40% of the monocytes form rosettes with at least 1 SRBC as determined by light microscopy, the candidate can be an opsonin.

Engineered Opsonins Containing a Lipid

The attachment of a lipid, e.g. a long-chain fatty acid, to a molecule, e.g. a polypeptide, can permit the complex to become stably associated with the plasma membrane when the complex is admixed with a cell (Nagarajan et al, 1995, J Immunol Methods 184:241–51; McHugh et al, 1995, PNAS 92:8059–63; van den Berg et al, 1995, J Cell Biol, 131:669–77). This is believed to occur through intercalation of the lipid into the membrane. A convenient method of producing a lipid-associated polypeptide comprises expressing, in a suitable host cell, a nucleic acid encoding, in part, a signal sequence directing the post-translational addition of a GPI moiety. Using recombinant DNA technology, a naturally non-GPI linked protein can be expressed as a GPI-linked protein by constructing a nucleic acid that encodes the protein linked to a heterologous GPI signal sequence. Nucleotide sequences encoding GPI signal sequences useful for this purpose include, for example, those comprised by decay accelerating factor (e.g., sequences encoding amino acid sequence "22" in Table 1 of Bucht and Hjalmarsson, 1996, Biochim Biophys Acta 1292:223–32; sequences encoding signal sequences disclosed in Caras et al, U.S. Pat. No. 5,109,113); brevican (e.g., nt 1982–2047 of Genbank accession number X86406), mesothelin (e.g., nt 1858–1983 of Genbank U40434), coccidioides immitis antigen 2 (e.g., sequences encoding amino acids 172–194 of NCBI Entrez protein database accession # 1256444, Zhu et al, 1996, Gene 181:121–5), acetylcholinesterase (e.g., sequences encoding the peptide "HC" as described in Duval et al, 1992., EMBO J 11:3255–61; (e.g., sequences encoding amino acid sequence "19" in Table 1 of Bucht and Hjalmarsson, 1996, Biochim Biophys Acta 1292:223–32)), human folate receptors alpha and beta (e.g., sequences encoding amino acids 230–257 of NCBI Entrez protein database accession # 182416 or amino acids 228–255 of NCBI Entrez protein database accession # 1655592, Yan and Ratnam, 1995, Biochemistry 34:14594–600), 5' nucleotidase (e.g., sequences encoding amino acids 547–570 or 547–574 of NCBI Entrez protein database accession # 404502, Furukawa et al, 1994, Biochim Biophys Acta 1190:273–8; (e.g., sequences encoding amino acid sequences "5" or "6" in Table 1 of Bucht and Hjalmarsson, 1996, Biochim Biophys Acta 1292:223–32)), CD59 (e.g. encoded by nt 393–473 of Genbank U48255; sequences encoding amino acid sequence "20" in Table 1 of Bucht and Hjalmarsson, 1996, Biochim Biophys Acta 1292:223–32; sequences encoding amino acids 74–101 of FIG. 2 of Powell et al, 1997, J Immunol 158:1692–1702), T-cadherin (e.g., sequences encoding the 76 C-terminal amino acids of chick T cadherin as described by Koller and Ranscht, 1996, J Biol Chem 271:30061–7), aminopeptidase P (e.g., sequences encoding amino acids 649–673 of NCBI Entrez protein database accession # 1517942, Hyde et al, 1996, Biochem J 319:197–201), carboxypeptidase M, CD16B, Thy 1, carbonic anhydrase IV (e.g., sequences encoding amino acids 284–312 of NCBI Entrez protein database accession # 179791, Okuyama et al, 1995, Arch Biochem Biophys 320:315–22), placental alkaline phosphatase (e.g ., sequences encoding amino acids 498–529 of NCBI Entrez protein database accession # 178464, Oda et al, 1994, Biochem J 301:577–83), neuronal glycoprotein F3, carcinoembryonic antigen (e.g., sequences encoding amino acid sequence "28" in Table 1 of Bucht and Hjalmarsson, 1996, Biochim Biophys Acta 1292:223–32), MRC-OX45 (e.g., sequences encoding amino acid sequence "2" in Table 1 of Bucht and Hjalmarsson, 1996, Biochim Biophys Acta 1292:223–32), RT 6.2 (e.g., sequences encoding amino acid sequence "3" in Table 1 of Bucht and Hjalmarsson, 1996, Biochim Biophys Acta 1292:223–32), *D. discoideum* prespore-specific antigen (e.g., sequences encoding amino acid sequence "4" in Table 1 of Bucht and Hjalmarsson, 1996, Biochim Biophys Acta 1292:223–32), microsomal dipeptidase (e.g., sequences encoding amino acid sequence "8" in Table 1 of Bucht and Hjalmarsson, 1996, Biochim Biophys Acta 1292:223–32), CAMPATH-1 (e.g., sequences encoding amino acid sequence "9" in Table 1 of Bucht and Hjalmarsson, 1996, Biochim Biophys Acta 1292:223–32), *T. brucei* PARP (e.g., sequences encoding amino acid sequence "10" in Table 1 of Bucht and Hjalmarsson, 1996, Biochim Biophys Acta 1292:223–32), *T. brucci* VSG Mit 118a (e.g., sequences encoding amino acid sequence "11" in Table 1 of Bucht and Hjalmarsson, 1996, Biochim Biophys Acta 1292:223–32), *T. brucei* VSG Mit 117a (e.g., sequences encoding amino acid sequence "12" in Table 1 of Bucht and Hjalmarsson, 1996, Biochim Biophys Acta 1292:223–32), *T. brucei* VSGMITat 1.1000 BC (e.g., sequences encoding amino acid sequence "13" in Table 1 of Bucht and Hjalmarsson, 1996, Biochim Biophys Acta 1292:223–32), *T. brucei* VSG MITat 1.5b (e.g., sequences encoding amino acid sequence "14" in Table 1 of Bucht and Hjalmarsson, 1996, Biochim Biophys Acta 1292:223–32), *T. brucei* VSG ILTat 1.1 (e.g., sequences encoding amino acid sequence "15" in Table 1 of Bucht and Hjalmarsson, 1996, Biochim Biophys Acta 1292:223–32), *T. brucei* VSG TxTat 1 (e.g., sequences encoding amino acid sequence "16" in Table 1 of Bucht and Hjalmarsson, 1996, Biochim Biophys Acta 1292:223–32), *T. brucei* VSG Mit 221 (e.g., sequences encoding amino acid sequence "17" in Table 1 of Bucht and Hjalmarsson, 1996, Biochim Biophys Acta 1292:223–32), prion proteins (e.g., sequences encoding amino acid sequence "18" in Table 1 of Bucht and Hjalmarsson, 1996, Biochim Biophys Acta 1292:223–32), urokinase receptor (e.g., sequences encoding amino acid sequence "21 " in Table 1 of Bucht and Hjalmarsson, 1996, Biochim Biophys Acta 1292:223–32), *T. congolense* VSG YNat 1.1 (e.g., sequences encoding amino acid sequence "23" in Table 1 of Bucht and Hjalmarsson, 1996, Biochim Biophys Acta 1292:223–32), *S. cerevesiae* GAS-1 (e.g., sequences encoding amino acid sequence "24" in Table 1 of Bucht and Hjalmarsson, 1996, Biochim Biophys Acta 1292:223–32), Thy-1 (e.g., sequences encoding amino acid sequences "25" or "26" in Table 1 of Bucht and Hjalmarsson, 1996, Biochim Biophys Acta 1292:223–32), L. major PSP (e.g., sequences encoding amino acid sequence "29" in Table 1 of Bucht and Hjalmarsson, 1996, Biochim Biophys Acta 1292:223–32), *D. discoideum* contact site A glycoprotein (e.g., sequences encoding the 25 C-terminal amino acids as described in Barth et al, 1996, Biochem J 317:533–40)CD24, and synthetic sequences (e.g. as described by Coyne et al, 1993, J Biol Chem 268:6689–93).

Determination of Binding of GPI-linked Opsonin to Cell According to the Invention In one embodiment of the invention, the opsonin is engineered so as to contain GPI or a moiety of GPI which contains a lipid and thus permits binding of the opsonin to a cell via intercalation of the lipid group into the plasma membrane of the cell. For those GPI moieties which consist of more or less than conventional GPI, one of skill in the art can easily determine whether such a moiety will permit binding of the opsonin to the cell membrane. The following assay is useful for determining whether a GPI-linked opsonin is able to bind to a cell.

To quantitate incorporation, GPI-linked opsonin is first labeled with $^{125}I$. Sephadex G-25 column is loaded with 0.1 mg of the relevant protein in 1 ml PBS, followed by 20–30 ml PBS. 2 mCi Na[$^{125}I$] and 20 ul of 10 uM lactoperoxidase in PBS are added to 2 ml of a 1 mg/ml solution of relevant protein in PBS. 4 ul of 0.03% hydrogen peroxide in 0.025 M phosphate buffer, pH 7.4, is stirred into the protein solution. Addition of hydrogen peroxide is repeated three more times at 1 min intervals. 1 ml of 15 nM NaI in PBS is added. The solution is layered onto the Sephadex column and eluted with 20 ml PBS. The eluant is monitored by Geiger counting, and the first peak of radioactivity, which contains the labeled protein, is collected. The specific activity is determined by gamma counting (assuming 100% recovery). The protein solution is diluted to 40 ug/ml and used for the plasma membrane incorporation procedure above. After washing, 1 ul aliquots of cells are gamma counted. To determine whether association is via the GPI moiety, cells are incubated with B. Thuringiensis phosphatidylinositol-specific phospholipase C (Sigma) at 37° C. for 3 hr, centrifuged, and washed prior to counting. This releases GPI-linked proteins from the cell surface.

Antigens Useful According to the Invention

1. Viral Antigens

Examples of viral antigens include, but are not limited to, retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS 1, NS 1, NS 1 -NS2A, 80% E, and other Japanese encephalitis viral antigen components; rabies viral antigens such as rabies glycoprotein, rabies nucleoprotein and other rabies viral antigen components. See Fundamental Virology, Second Edition, e's. Fields, B.N. and Knipe, D.M. (Raven Press, New York, 1991) for additional examples of viral antigens.

2. Bacterial antigens

Bacterial antigens which can be used in the compositions and methods of the invention include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diphtheria bacterial antigen components; tetanus bacterial antigens such as tetanus toxin or toxoid and other tetanus bacterial antigen components; streptococcal bacterial antigens such as M proteins and other streptococcal bacterial antigen components; gram- negative bacilli bacterial antigens such as lipopolysaccharides and other gram-negative bacterial antigen components; Mycobacterium tuberculosis bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; hemophilus influenza bacterial antigens such as capsular polysaccharides and other hemophilus influenza bacterial antigen components; anthrax bacterial antigens such as anthrax protective antigen and other anthrax bacterial antigen components; rickettsiae bacterial antigens such as romps and other rickettsiae bacterial antigen component. Also included with the bacterial antigens described herein are any other bacterial, mycobacterial, mycoplasmal, rickettsial, or chlamydial antigens.

3. Fungal antigens

Fungal antigens which can be used in the compositions and methods of the invention include, but are not limited to, candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

4. Parasite antigens

Examples of protozoa and other parasitic antigens include, but are not limited to, plasmodium falciparum antigens such as merozoite surface antigens, sporozoite surface antigens, circumsporozoite antigens, gametocyte/ gamete surface antigens, blood-stage antigen pf 1 55/RESA and other plasmodial antigen components; toxoplasma antigens such as SAG-1, p30 and other toxoplasma antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75–77 kDa antigen, the 56 kDa antigen and other trypanosomal antigen components.

5. Tumor antigens.

Tumor antigens which can be used in the compositions and methods of the invention include, but are not limited to, telomerase; multidrug resistance proteins such as P-glycoprotein; MAGE-1, alpha fetoprotein, carcinoembryonic antigen, mutant p53, papillomavirus antigens, gangliosides or other carbohydrate-containing components of melanoma or other tumor cells. It is contemplated by the invention that antigens from any type of tumor cell can be used in the compositions and methods described herein.

6. Antigens relating to autoimmunity.

Antigens involved in autoimmune diseases, allergy, and graft rejection can be used in the compositions and methods of the invention. For example, an antigen involved in any one or more of the following autoimmune diseases or disorders can be used in the present invention: diabetes mellitus, arthritis (including rheumatoid arthritis, juvenile rheumatoid arthritis, osteoarthritis, psoriatic arthritis), multiple sclerosis, myasthenia gravis, systemic lupus erythematosus, autoimmune thyroiditis, dermatitis (including atopic dermatitis and eczematous dermatitis), psoriasis, Sjogren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. An antigen can also be an altered peptide ligand useful in treating an autoimmune disease.

Examples of miscellaneous antigens which can be can be used in the compositions and methods of the invention include endogenous hormones such as luteinizing hormone, follicular stimulating hormone, testosterone, growth hormone, prolactin, and other hormones, drugs of addiction such as cocaine and heroin, and idiotypic fragments of antigen receptors such as Fab-containing portions of an anti-leptin receptor antibody.

Preparation of a Cell Containing a Recombinant Nucleic Acid According to the Invention Cells are transfected, as taught herein, via conventional methods well-known in the art. Suitable methods for transforming or transfecting host cells can be found in Sambrook et al. (*Molecular Cloning: A Laboratory Manual,* 2nd Edition, Cold Spring Harbor Laboratory press (1989)), and other laboratory manuals. Additional examples of methods of introducing nucleic acid molecules encoding opsonins are described below. The cells containing the introduced nucleic acid molecules encoding, for example, an opsonin and/or an antigen, can themselves be administered to a subject (as the antigen) according to the methods of the invention, e.g., in a vaccine composition.

A. Introduction of Naked Nucleic Acid into Cells

1. Transfection mediated by DEAE-dextran: Naked nucleic acid can be introduced into cells by forming a mixture of the nucleic acid and DEAE-dextran and incubating the mixture with the cells. A dimethylsulfoxide or chloroquine shock step can be added to increase the amount of nucleic acid uptake. DEAE-dextran transfection is only applicable to ice vitro modification of cells and can be used to introduce nucleic acid transiently into cells but is not preferred for creating stably transfected cells. Thus, this method can be used for short term production of a gene product but is not a method of choice for long-term production of a gene product. Protocols for DEAE-dextran-mediated transfection can be found in *Current Protocols in Molecular Biology,* Ausubel, F.M. et al. (e's.) Greene Publishing Associates, (1989), Section 9.2 and in *Molecular Cloning: A Laboratory Manual.* 2nd Edition. Sambrook et al. Cold Spring Harbor Laboratory Press, (1989), Sections 16.41–16.46 or other standard laboratory manuals.

2. Electroporation: Naked nucleic acid can also be introduced into cells by incubating the cells and the nucleic acid together in an appropriate buffer and subjecting the cells to a high-voltage electric pulse. The efficiency with which nucleic acid is introduced into cells by electroporation is influenced by the strength of the applied field, the length of the electric pulse, the temperature, the conformation and concentration of the nucleic acid and the ionic composition of the media. Electroporation can be used to stably (or transiently) transfect a wide variety of cell types and is only applicable to in vitro modification of cells. Protocols for electroporating cells can be found in *Current Protocols in Molecular Biology*, Ausubel, F.M. et al. (e's.) Greene Publishing Associates, (1989), Section 9.3 and in *Molecular Cloning: A Laboratory Manual*, 2nd Edition, Sambrook et al. Cold Spring Harbor Laboratory Press, (1989), Sections 16.54–16.55 or other standard laboratory manuals.

3. Liposome-mediated transfection ("lipofection"): Naked nucleic acid can be introduced into cells by mixing the nucleic acid with a liposome suspension containing cationic lipids. The nucleic acid/liposome complex is then incubated with cells. Liposome mediated transfection can be used to stably (or transiently) transfect cells in culture in vitro. Protocols can be found in *Current Protocols in Molecular Biolog*, Ausubel, F.M. et al. (e's.) Greene Publishing Associates, (1989), Section 9.4 and other standard laboratory manuals. Additionally, gene delivery in vivo has been accomplished using liposomes. See for example Nicolau et al. (1987) *Meth. Enz.* 149:157–176; Wang and Huang (1987) *Proc. Natl. Acad Sci. SA* 84:7851–785S; Brigham et al. (1989) *Am. J Med. Sci.* 298:278; and Gould-Fogerite et al. (1989) *Gene* 84:429–438.

4. Direct Injection: Naked nucleic acid can be introduced into cells by directly injecting the nucleic acid into the cells. For an in vitro culture of cells, nucleic acid can be introduced by microinjection. Since each cell is microinjected individually, this approach is very labor intensive when modifying large numbers of cells. However, a situation wherein microinjection is a method of choice is in the production of transgenic animals (discussed in greater detail below). In this situation, the nucleic acid is stably introduced into a fertilized oocyte which is then allowed to develop into an animal. The resultant animal contains cells carrying the nucleic acid introduced into the oocyte. Direct injection has also been used to introduce naked nucleic acid into cells in vivo (see e.g., Acsadi et al. (1991) *Nature* 332: 815–818; Wolff et al. (1990) *Science* 247:1465–1468). A delivery apparatus (e.g., a "gene gun") for injecting DNA into cells in vivo can be used. Such an apparatus is commercially available (e.g., from BioRad).

5. Receptor-Mediated DNA Uptake: Naked nucleic acid can also be introduced into cells by complexing the nucleic acid to a cation, such as polylysine, which is coupled to a ligand for a cell-surface receptor (see for example Wu, G. and Wu, C.H. (1988) *J Biol. Chem* 263:14621; Wilson et al. (1992) *J Biol. Chem.* 267:963–967; and U.S. Pat. No. 5,166,320). Binding of the nucleic acid-ligand complex to the receptor facilitates uptake of the nucleic acid by receptor-mediated endocytosis. Receptors to which a nucleic acid-ligand complex have targeted include the transferrin receptor and the asialoglycoprotein receptor. A nucleic acid-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Nati. Acad. Sci. USA* 88:8850; Cristiano et al. (1993) *Proc. Natl. Acad. Sci USA* 90:2122–2126). Receptor-mediated nucleic acid uptake can be used to introduce nucleic acid into cells either in vitro or in vivo and, additionally, has the added feature that nucleic acid can be selectively targeted to a particular cell type by use of a ligand which binds to a receptor selectively expressed on a target cell of interest.

Generally, when naked nucleic acid is introduced into cells in culture (e.g., by one of the transfection techniques described above) only a small fraction of cells (about 1 out of 105) typically integrate the transfected nucleic acid into their genomes (i.e., the nucleic acid is maintained in the cell episomally). Thus, in order to identify cells which have taken up exogenous nucleic acid, it is advantageous to transfect nucleic acid encoding a selectable marker into the cell along with the nucleic acid(s) of interest. Preferred selectable markers include those which confer resistance to drugs such as G418, hygromycin and methotrexate. Selectable markers may be introduced on the same plasmid as the gene(s) of interest or may be introduced on a separate plasmid.

B. Viral-Mediated Gene Transfer

A preferred approach for introducing nucleic acid encoding a gene product into a cell is by use of a viral vector containing nucleic acid, e.g. a cDNA, encoding the gene product. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are expressed efficiently in cells which have taken up viral vector nucleic acid and viral vector systems can be used either in vitro or in vivo.

1. Retroviruses: Defective retroviruses are well characterized for use in gene transfer for gene therapy purposes (for a review see Miller, A.D. (1990) *Blood* 76:271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F.M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include $_{13}$ Crip,$_{13}$ Cre,$\_$2, and$_{13}$ Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad Sci. USA* 88:8377–8381; Chowdhury et al. (1991) *Science* 254:1802–1805; van Beusechem et al. (1992) *Proc. Natl. Acad Sci. USA* 89:7640–7644; Kay et al. (1992) *Human Gene Therapy* 3:641–647; Dai et al. (1992) *Proc. Natl. Acad Sci. USA* 89:10892–10895; Hwu et al.

(1993) *J Immunol.* 150:4104.–115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

2. Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Adz, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral nucleic acid (and foreign DNA contained therein) is not integrated into the genome of a host cell but remains episomal, thereby avoiding potential problems that can occur as a result of insertional mutagenesis in situations where introduced nucleic acid becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J Virol.* 57:267). Most replication-defective adenoviral vectors currently in use are deleted for all or parts of the viral E1 and E3 genes but retain as much as 80% of the adenoviral genetic material.

3. Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J Respir. Cell. Mol. Biol.* 7:349–356; Samulski et al. (1989) J. Virol. 63:3822–3828; and McLaughlin et al. (1989) *J Virol* 62:1963–1973). Vectors containing as little as 300 base pairs of AAV can be packaged and can integrate. Space for exogenous nucleic acid is limited to about 4.5 kb. An AAV vector such as that described in Tratschin et al. (1985) *Mol. Cell. Biol.* 5:3251–3260 can be used to introduce nucleic acid into cells. A variety of nucleic acids have been introduced into different cell types using AAV vectors (see for example Hermonat et al. (1984) *Proc. Natl. Acad. Sci. USA* 81 :6466–6470; Tratschin et al. (1985) *Mol. Cell. Biol.* 4:2072–2081; Wondisford et al. (1988) *Mol. Endocrinol.* 2:32–39; Tratschin et al. (1984) *J Virol.*51 :611–619; and Flotte et al. (1993) *J Biol. Chem.* 268:3781–3790).

The efficacy of a particular expression vector system and method of introducing nucleic acid into a cell can be assessed by standard approaches routinely used in the art. For example, nucleic acid introduced into a cell can be detected by a filter hybridization technique (e.g., Southern blotting) and RNA produced by transcription of introduced nucleic acid can be detected, for example, by Northern blotting, RNase protection or reverse transcriptase-polymerase chain reaction (RI-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product which is easily detectable and, thus, can be used to evaluate the efficacy of the system. Standard reporter genes used in the art include genes encoding $_{13}$-galactosidase, chloramphenicol acetyl transferase, luciferase and human growth hormone.

Preparation of Cells in Admixture with an Opsonin According to the Invention

The invention also contemplates a preparation of cells that is admixed with a opsonin or an opsonin. Therefore, the cell may already express an antigen, for example, a tumor cell antigen (either an endogenously expressed antigen or a heterologous antigen), and may be mixed with an opsonin, as defined hereinabove, and the preparation considered to be "opsonin-enhanced cells" according to the invention. In this mixture, the preparation will consist of about $10^4$–$10^8$ cells mixed with 1 ug-100 ug/ml protein (opsonin) in a conventional physiological salt buffer.

Where the invention encompasses a preparation of cells in admixture with an opsonin, the opsonin is first prepared according to conventional procedures and then mixed with the cells. The opsonin may be prepared via recombinant DNA techniques via transfection of a host cell strain or line and isolation of the recombinant protein.

A host cell of the invention, such as a eukaryotic host cell in culture, can be used to produce (i.e., express) polypeptides of the invention. For example, a transfected host cell (into which a recombinant expression vector encoding a polypeptide of the invention has been introduced) may be cultured in a suitable medium until the polypeptide is produced, and isolated from the medium or the host cell.

Transfection mediated by CaPO4: Naked nucleic acid can be introduced into cells by forming a precipitate containing the nucleic acid and calcium phosphate. For example, a HEPES-buffered saline solution can be mixed with a solution containing calcium chloride and nucleic acid to form a precipitate and the precipitate is then incubated with cells. A glycerol or dimethyl sulfoxide shock step can be added to increase the amount of nucleic acid taken up by certain cells. CaPO4-mediated transfection can be used to stably (or transiently) transfect cells and is only applicable to in vitro modification of cells. Protocols for CaPO4-mediated transfection can be found in *Current Protocols in Molecular Biology*, Ausubel, F.M. et al. (eds.) Greene Publishing Associates, (1989), Section 9.1 and in *Molecular Cloning: A Laboratory Manual.* 2nd Edition. Sambrook et al. Cold Spring Harbor Laboratory Press, (1989), Sections 16.32–16.40 or other standard laboratory manuals.

Determining Whether an Immune Response is Modulated Accordins to the Invention

Opsonin-enhanced cells are useful according to the invention to modulate an immune response in a mammalian, preferably a human, to an antigen or antigens contained in the cells. The cells are administered and are taken up (i.e., ingested or phagocytosed) by antigen presenting cells. Alternatively, the cells are contacted with antigen presenting cells in vitro under conditions which allow phagocytosis.

An "immune response" refers to stimulation/activation of a selected response involving the immune system, or suppression, elimination, or attenuation of a selected response. Thus, to modulate an immune response means that the desired response is more efficient, more rapid, greater in magnitude, and/or more easily induced than when cells, identical in every respect except that they are not opsonin-enhanced cells, are administered in an identical fashion. Different immune responses in the subject may be modulated differentially, e.g., the cellular immune response may be selectively enhanced while the humoral response may be selectively attenuated, and vice versa.

The following in in vitro and in vivo assays are useful for determining whether an immune response is modulated according to the invention. The assays described in detail below measure stimulation or suppression of cellular or humoral immune responses to an antigen. The antigens referred to in the following assays are representative. It will be apparent to one of skill in the art that an immune response to a selected antigen useful according to the invention may be measured using one or more of the following assays by adapting the assay to that antigen.

I. Detection of Increased Phagocytosis

The following assay may be used in order to determine whether opsonin-enhanced cells stimulate phagocytosis by antigen presenting cells.

Phagocytosis is examined using monocytes that have been adhered at 37° for 30 min in RPMI without added FCS. Sheep erythrocytes are incubated with a candidate opsonin, or its precursor, under conditions such that there are no more than 300 of such molecules, on average, are deposited on each erythrocyte. If a precursor is used, coated erythrocytes are then processed to convert all precursors to the actual candidate molecule (e.g., See Carlo et al., J. Immunol. 123:523–8(1979)). Fresh monocytes are isolated from the subject, and $5 \times 10^4 - 1 \times 10^5$ of these cells suspended in 0.25–0.5 ml of RPMI medium with 1% BSA. This aliquot is placed in a tissue culture well and incubated for 30 min at 37° C. An excess of coated erythrocytes, suspended at $1.2 \times 10^8$ cells/ml, is overlain on the monocytes, the plate is centrifuged for 5 min at 50 g, and incubated for 30 min at 37° C. Non- ingested material is removed in two hypotonic lysis steps using ice-cold lysing buffer before fixing and staining the adherent cells, and examining the cells under light microscopy. Phagocytosis is quantified by determining the percentage of 100 monocytes ingesting one or more target cells, and the total number of ingested E/100 monocyptes (PI) is recorded. Stimulation of phagocytosis according to the invention is indicated by a phagocytic index of equal to or greater than 40.

II. Amplification of the immune response usually involves proliferation of particular subpopulations of lymphoid cells that are normally in the resting state.

Proliferative assays have the following applications in clinical studies: (1) Assessment of overall immunologic competence of T cells or B cells as manifested in their ability to respond to polyclonal proliferation signals such as mitogens or anti-CD3 antibodies. Defects in the proliferation may be indicative of fundamental cellular immunologic defect. Low proliferation is often found as a nonspecific secondary effect of chronic disease. (2) Assessment of an individual's response to specific antigens, where low responses are indicative of general or specific immunologic defect. (3) Determination of MHC compatibility by the mixed lymphocyte reaction (MLR).

In addition, proliferative assays are useful for estimating lymphokine production, investigating signal transduction, and assessing growth factor requirements (e.g., lymphokines) for T or B cells. The procedure outlined here measures incorporation of [$^3$H]thymidine into DNA, which usually correlates well with cell growth as measured by changes in cell number. However, when the activation stimulus is toxic, as with chemical activators such as ionomycin plus phorbol myristate acetate (PMA), the burst of new DNA synthesis following activation may not be accompanied with a net increase in viable cells, and, in fact, a decline in cell number may be observed. In this instance, [$^3$H]thymidine incorporation in DNA is more indicative of initial cell stimulation than estimation of cell number. In addition, [$^3$H]thymidine incorporation provides information on cell populations, not on individual cells. Alternate methods, such as flow cytometry may be used for studies requiring that type of information.

Assay For Antigen-Induced T Cell Proliferation

This protocol is designed to test the proliferation of T cells in response to a specific antigen-tetanus toxoid. It can be modified to test T cell proliferation in response to any protein or polysaccharide antigen. Materials: (T cell suspension, autologous antigen-presenting cell suspension (non-T cells), Tetanus toxoid solution (Connaught or State Laboratory Institute of Massachusetts)). (1) Count T cells and adjust to $1 \times 10^6$ cells/ml with complete RPMI-10 AB. (2) Treat antigen-presenting cells with mitomycin C (or irradiate with 2500 rad) as in step 2 of one-way MLR protocol. Adjust concentration of antigen-presenting cells to $2 \times 10^5$ cells/ml. Antigen-presenting cells can consist of autologous non-T cells or autologous monocytes/ macrophages. (3) Add 100 ul T cell suspension and 50 ul antigen-presenting cell population to wells; mix just before dispensing. (4) Add 50 ul tetanus toxoid solution to give final concentrations of 0, 1, 5, 10, and 20 ug/ml. Prepare three wells for each dilution. (5) Incubate 6 days in a humidified 37° C., 5% $CO_2$ incubator. (6) Pulse with [$^3$H]thymidine and harvest as described in support protocol.

Assay For Lymphokine-Dependent Cell Proliferation

This protocol assays the lymphokine-dependent proliferation of a lymphocyte population, in this case, the IL-4 dependent proliferation of B cells. Materials: (Tonsil B cell suspension, Anti-IgM cross-linked to Sepharose beads (Bio-Rad), 10,000 U/ml human rIL-4 (Genzyme) in complete RPMI-10). (1) Count tonsil B cells and adjust concentration to $1 \times 10^6$ cells/ml with complete RPMI-10. (2) Dispense 100 ul of tonsil B cells into each well. Prepare three wells for each experimental condition. (3) Dilute 10,000 U/ml rIL-4 solution 1.10, 1:100, and 1:1000. Add 20 ul of the stock or dilution to appropriate wells to yield 1000 U/ml, 100 U/ml, 10 U/ml, and 1 U/ml. Include a control well with no rIL-4. (4) Pipet anti-IgM beads into appropriate wells.

Determine the optimal concentration of beads with pilot experiments. It is best to include several concentrations of beads in each experiment to "bracket" the optimal dose. Prepare wells with tonsil B cells and IL-4 dilutions alone, anti-IgM beads alone, culture medium alone, and all the combinations of IL-4 and anti-IgM bead dilutions. (5) Increase the volume of each well to 200 ul with complete RPMI-10 as necessary. (6) Culture 5 days in a humidified 37° C., 5% $CO_2$ incubator. (7) Pulse with [$^3$H]thymidine and harvest as described in support protocol.

[$^3$H]Thymidine Pulse And Harvest Of Cell Cultures

This protocol is used in conjunction with the preceding protocols to complete the [$^3$H] thymidine incorporation assay. (1) Add 20 ul of 50 uCi/mi [$^3$H]thymidine to each culture (1.0 uCi) at a fixed time before terminating the culture (usually 6 or 18 hr). (2) Harvest cell cultures using an automated multiwell harvester that aspirates cells, lyses cells, and transfers DNA onto filter paper, while allowing unincorporated [$^3$H]thymidine to wash out. Fill and aspirate each row of the microtiter plate ten times to ensure complete cell transfer and complete removal of unincorporated thymidine. Wash each filter strip with 100% ethanol to facilitate drying. Transfer to scintillation vials. For semiautomated harvester, transfer filter dots for each well into scintillation counting vials. For manual transfer, dry filters under lamp and transfer to scintillation vial with forceps. Add scintillation fluid to each vial. (3) Count samples in scintillation counter until standard deviation is less than 2%. Calculate mean cpm for background cultures and for each experimental condition. There should be less than 20% variation in replicate cultures.

III. Induction And Measurement Of In Vitro Antibody Responses

The capacity of the human immune system to mount an antibody response following in vivo immunization with a protein or polysaccharide antigen is a revealing indication of the overall integrity of both the B and T cell arms of the immune system. As such, in vivo immunization followed by measurement of the antibody response is an appropriate test of immune function in the various acquired and congenital immunodeficiencies and in a host of other conditions affecting the immune system. The following procedures are for in vivo immunization and for the measurement of the subsequent immune response using an ELISA technique.

Immuno-Enzymetric Assay For Cytokines Using NIP- And HRPO-Labeled Antibodies

This protocol describes an immunonoenzymetric assay for cytokines using a heterogeneous, noncompetitive immunoassay reaction in which the cytokine is immobilized by a coating antibody bound to a microtiter plate. Unbound material is washed free, and detection is carried out using a different anti-cytokine antibody labeled with the hapten nitroiodophenyl (NIP). This is in turn detected by a horseradish peroxidase (HRPO) conjugate of an anti-NIP antibody, which is revealed with the chromogenic substrate ABTS. In this noncompetitive immunoassay, the immunoassay signal ($A_{405}$) increases as a direct function of the amount of cytokine present in the sample. Antibodies are prepared as described in Current Protocols in Immunology, 1995, 6.20.2–6.20.10.

Coat assay plate. (1) Using a multichannel pipettor, transfer 100 ul of an appropriate dilution of coating antibody into all wells of the assay plate that are to be used. (2) Seal plates with microtiter plate sealer or Parafilm and incubate 2 hr. At 37° C. Prepare samples and standards in preparation plate. (3) Dilute each sample (or aliquot of conditioned medium) to be assayed with an equal volume of immunoassay diluent. (4) Pipet less than or equal to 1 ml of each diluted sample to be assayed into the upper chamber of a separate Spin-X microfiltration device. Microcentifuge 5 min. At 10,000 rpm and save the filtrates that collect in the lower chambers. (5) Add 65 ul of each diluted sample to the appropriate well of a preparation plate (i.e., a separate 96-well microtiter plate). (6) Thaw an aliquot of cytokine standard at room temperature and make sure that it is well mixed. Pipet 130 ul into the well of the preparation plate representing the highest concentration on the standard curve. Transfer 65 ul from this well into the next, then continue performing serial 1:1 dilutions in immunoassay diluent so that 65 ul of each concentration represented on the standard curve is placed in appropriate well of the preparation plate. (7) Thaw an aliquot of calibrator at room temperature (if used). Dilute with an equal volume of immunoassay diluent, then pipet 65 ul of diluted calibrator into appropriate well or wells of preparation plate.

Incubate with coating antibody. (8) Remove coated assay plate from incubator. Dip in 2-liter beaker filled with 1×wash buffer, then invert over sink and flick to remove liquid. Repeat two more times, then bang dry on paper towel. (9) Transfer 50 ul of solution from each well of preparation plate to corresponding well of the assay plate using multichannel pipettor. (10) Seal plate with microtiter plate sealer or Parafilm and incubate 2 hr. at room temperature.

Incubate with detecting antibody. (11) Dilute NIP-labeled detecting antibody specific to cytokine of interest to 1 ug/ml in detecting buffer. (12) Wash assay plate as in step 8. (13) Add 75 ul diluted detecting antibody from step 11 to all wells of assay plate, including unused outer walls. (14) Reseal plate with microtiter plate sealer or Parafilm and incubate 1 hr. at room temperature.

Incubate with HRPO-conjugated anti-NIP antibody. (15) Dilute HRPO-conjugated anti-NIP Mab 1:3000 in detecting buffer. (16) Wash assay plate as in step 8. (17) Add 75 ul of diluted HRPO-labeled anti-NIP antibody from step 15 to all wells of assay plate. (18) Reseal plate with microtiter plate sealer or Parafilm and incubate 1 hr. at room temperature.

Incubate with chromogenic substrate. (19) Wash assay plate as in step 8. (20) Add 100 ul ABTS substrate working solutions to all wells of assay plate. Cover plate and incubate at room temperature until color development reaches desired level (generally until $A_{405}$ for wells containing the highest concentration of standard is between 1.5 and 2). This protocol usually produces an assay that can be read after 30 to 60 min.

Read plate and analyze data. (21) Using microtiter plate reader with computer interface, measure absorbance in all wells at 405 nm in single-wavelength mode or at 405 and 650 nm in dual-wavelength mode. (22) Fit standard data to a curve described by a first-degree (linear), second degree (quadratic), or four-parameter (nonlinear) mathematical function using curve-fitting software. (23) Interpolate absorbance data from unknown cytokine samples to fitted standard curve, and calculate cytokine concentrations.

IV. Induction of an in vivo antibody response provides an approach to the evaluation of the overall integrity of the immune system. In the protocols presented here, diptheria and tetanus toxoids are used as representative protein antigens and pneumococcal polysaccharides are used as representative polysaccharide antigens because of their safety and availability. It should be noted, however, that the responses elicited by these antigens are likely to be secondary responses because of past vaccination or natural exposure. To obtain a primary response, an unusual antigen such as keyhole limpet hemocyanin should be used.

When antigens are administered by the intramuscular or subcutaneous route, as they are here, a "systemic" immune response is induced and measurement of circulating antibody is most appropriate. It is, however, sometimes of interest to evaluate "local" or mucosal immune responses. In this case, the antigen is given either intranasally to stimulate respiratory lymphoid tissue or orally to stimulate gastrointestinal lymphoid tissue and bronchial washings or intestinal fluids, rather than blood, is assayed for antibody content; in addition, antigens are used that are more appropriate for stimulation of the local/mucosal response (i.e., influenza virus antigen for respiratory responses and cholera toxin for gastrointestinal responses).

In assaying the in vivo antibody response, it is important to determine responses to both protein and polysaccharide antigens because these antigens stimulate different components of the immune system. In this regard, the major antibody response to protein antigen is composed of IgG1 and IgG3 subclass antibodies, whereas the major antibody response to polysaccharide antigen is composed of IgG2 subclass antibody.

A variety of immunoassay techniques have been used to measure antibody responses in materials obtained after in vivo immunization. Of these, the ELISA assay is perhaps the most useful because it yields a stable, easily measurable, reproducible, and safe readout.

Induction Of In Vivo Antibody Responses To Protein/Polysaccharide Antigens

In this protocol antigens are administered by the intramuscular or subcutaneous route and serum is collected for measurement of responses. (1) Draw preimmunized blood sample, allow blood to clot, and separate serum from clot by centrifugation. Store serum at −20° C. to −70° C. in appropriately labeled plastic tubes. (2) Inject 0.5 ml of toxoid mixture into an appropriately prepared intramuscular site (deltoid or thigh), taking care not to inject material intravenously. (3) Inject 0.5 ml polyvalent pneumococcal vaccine into an appropriately prepared subcutaneous site, taking care not to inject material intravenously. (4) Draw postimmunization blood samples at desired intervals, usually at 1, 2, and 3 weeks. Separate serum and store at −20° C. to −70° C. (5) After all serum samples are collected, assay samples for presence of antibodies using ELISA.

The ELISA offers a rapid, sensitive, reproducible, nonradioactive method for measuring in vivo antibody responses to a variety of antigens, including protein and polysaccharide antigens in sera obtained from individuals vaccinated with tetanus and diphtheria boosters and the polyvalent pneumococcal polysaccharide vaccine. Assays specific for tetanus, diphtheria and the pneumococcal polysaccharide types I, II, and III are detailed in Current Protocols in Immunology, 1995, Vols. 6 and 7.

Assay Using Tumor Rejection

In another assay for immunomodulation, an immunocompent animal is vaccinated with on the order of $10^4$–$10^8$ irradiated opsonin-enhanced tumor cells, and challenged with on the order of $10^4$–$10^8$ live wild-type tumor cells (in any temporal sequence). If survival or tumor onset in these animals differs from that of animal vaccinated, using identical parameters, with irradiated non-opsonin enhanced cells instead of opsonin-enhanced cells, immunomodulation has occurred. For example, if at least 10% of the animals in the test group survive 100% longer than mean survival in the control group, the test is positive. As another example, onset of tumors in 20% of the test animals might be 50% later than mean onset in the control animals.

Use

Tumors for which the Invention is Applicable

The invention contemplates treatment of tumors including but not limited to the following: Melanomas, squamous cell tumors, basal cell carcinomas, astrocytomas, gliomas, glioblastoma multiforme, meningiomas, ependymomas, schwannomas, neuroblastomas, retinoblastomas, meningiomas, glomus tumors, sarcomas, including, e.g., osteosarcomas, Ewing's sarcomas, chondrosarcomas, myosarcomas, synovial cell sarcomas, fibrosarcomas, spindle cell tumors, angiosarcomas, primitive neuroectodermal cell tumors, and Kaposi's sarcomas, lymphomas, acute and chronic leukemias, tumors of the head and neck, nasopharyngeal carcinomas, carcinomas of the pharynx, laryngeal carcinomas, carcinomas of the thyroid, carcinomas of the parathyroids, thymomas, esophageal carcinomas, gastric carcinomas, tumors of the small bowel, carcinomas of the colon and rectum, mesotheliomas, lung carcinomas, including adenocarcinomas, squamous cell carcinomas, bronchoalveolar carcinomas, and small cell tumors, pancreatic carcinomas, islet cell and non-islet cell tumors, carcinomas of the breast, cardiac myxomas, pituitary tumors, carcinoid tumors, hepatomas, cholangiocarcinomas, hepatoblastomas, renal cell carcinomas, nephroblastomas, Wilms' tumors, adrenal carcinomas, pheochromocytomas, germ cell tumors, choriocarcinomas, ovarian carcinomas, testicular tumors, seminomas, endometrial tumors, carcinomas of the prostate, carcinomas of the seminal vesicles, vaginal tumors, carcinomas of the penis, hydatiform moles, carcinomas of the gall bladder, and carcinomas of the urinary bladder.

Transgenic Animals According to the Invention

A nucleic acid molecule encoding an engineered opsonin as described herein can be used to produce nonhuman transgenic animals, and cells of such transgenic animals can be isolated and used in a vaccine formulation in animal or human vaccination.

For example, in one embodiment, a nucleic acid molecule is introduced into a fertilized oocyte or an embryonic stem cell. Such cells can then be used to create non-human transgenic animals in which exogenous nucleic acid molecules encoding the polypeptides of the invention have been introduced into their genome or homologous recombinant animals in which endogenous nucleic acid molecules have been altered. Such animals are useful for studying the function and/or activity of the molecules of the invention and for identifying and/or evaluating modulators of the activity of the molecules of the invention. As used herein, a "transgenic animal" is a non-human animal, prefers mammal, more preferably a mouse, in which one or more of the cells of the animal includes a transgene. A transgene is exogenous nucleic acid which is integrated into the genome of a cell from which a transgenic animal develops and which remains in the genome of the mature animal, thereby directing the expression of an encoded gene product in one or more cell types or tissues of the transgenic animal.

A transgenic animal of the invention can be created by introducing nucleic acid molecules encoding the polypeptides described herein into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of a polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the nucleic acid molecule of the invention, e.g., the transgene in its genome and/or expression of the transgene mRNA in tissues or cells of the animals. A transgenic founder animal can then be used to breed additional animals carrying the transgene. Moreover, transgenic animals carrying a transgene encoding polypeptides of the invention can further be bred to other transgenic animals carrying other transgenes.

The invention is further illustrated by the following exemplifications which should not be construed as being further limiting.

Preparation of Opsonin-Enhanced Opsonin-Expressing Cells

EXAMPLE 1

Opsonin-enhanced cells comprising murine tumor cells expressing the alpha' chain of murine C3b were generated as follows.

A sequence encoding the alpha' chain of murine C3b was cloned by PCR from mouse liver cDNA using an upstream primer corresponding to nucleotides 2304–2324 of Genbank K02782 and a downstream primer complementary to nt 5027–5050 of K02782 and incorporating a 5' Bcl I extension. The product was digested with BclI. The gene was ligated into a mammalian expression plasmid SFG (Dranoff et al. 1993, Proc. Nat. Aca. Sci. 90(8)3539), which incorporates a sequence encoding a polypeptide secretory sequence, such that the 5' blunt end of the C3ba' gene was attached to the free blunt upstream end of the vector and the 3' staggered end of C3ba' annealed and attached to the complementary staggered BclI overhand on the free downstream end of the vector.

For some experiments, the SFG-C3ba' plasmid was used to transfect amphotrophic transient retroviral producer cells (Bing cells, Pear et al., 1993, Proc. Nat. Acad. Sci. 90(16) 8392) using the calcium chloride method. Supernatants from these cells were used to introduce the C3b gene into murine B16 melanoma cells using the methods described in Pear et al., supra. These B16 cells were allowed to expand in culture until a sufficient number for in vivo experiments were obtained.

EXAMPLE 2

For other experiments, the SFG-C3ba' plasmid was coelectroporated with the selectable marker pSVneo directly into B16 melanoma or CMS-5 fibrosarcoma cells. These cells were selected and expanded for use as vaccines.

EXAMPLE 3

For other experiments, the murine mannose binding protein A gene was amplified from mouse liver cDNA using an upstream primer corresponding to nt 124–148 of Genbank S42292, and a downstream primer complementary to nt 817–840 of S42292 and incorporating a 5= Bgl II extension. This product was digested with Bgl II and ligated into an SFG plasmid with a blunted upstream Nco I and a staggered downstream Bam HI end (which is compatible with a Bgl II overhang). The plasmid was coelectroporated with pSVneo into psi-CRIP amphotrophic retroviral producer cells, and clones selected and expanded. Supernatants from these cells were used to transfer the MBP-A gene into B16 cells.

Vaccination Using Opsonin-enhanced Cells and Demonstration of Effectiveness of Opsonin-enhanced Cells

EXAMPLE 4

In one experiment, the ability of B16 cells transduced with GM-CSF was compared with the ability of a mixture of these cells and the C3ba'-transduced cells described above to act as a therapeutic vaccine against a wild-type B16 melanoma.

Nine C57B1/6 mice were each challenged with $1\times10^6$ live wild-type B16 cells, suspended in 0.5 ml HBSS; cells were injected subcutaneously in the neck region. Seven days later, 5 mice were vaccinated subcutaneously in the abdomen with $5\times10^5$ irradiated GM-CSF-transduced B16 cells in 0.5 ml HBSS (Dranoff et al, op. cit.). 4 mice were vaccinated with a mixture of $2.5\times10^5$ irradiated GM-CSF- transduced cells and $2.5\times10^5$ irradiated C3ba' transduced cells. The results were as follows. All 5 mice that received GM-CSF cells alone developed tumors on day 9 after challenge. Of the mice that received the mixed vaccine, 1 mouse developed a tumor on day 9, one on day 12, one on day 51, and one had not developed a tumor by day 180. No mouse in the GM-CSF set survived past day 20, while all in the mixed set survived to at least day 30.

In these experiments, each mouse was sacrificed if and when its tumor became unwieldy. Although this involves some subjective evaluation, conscientious attempts were made to be consistent in terms of the size of tumors at the time of sacrifice. For example, mice were sacrificed when tumor weight appeared to exceed 15–20% of body weight, or when ambulation was affected.

EXAMPLE 5

In another experiment, the ability of wild-type B16 cells to act as a preventive vaccine against tumor formation was compared to that of B16 cells transduced with C3ba'. 5 C57BL/6 mice were vaccinated with $5\times10^5$ irradiated wild-type cells subcutaneously in the abdomen, and 5 mice were vaccinated with $5\times10^5$ irradiated C3ba'-transduced cells. Seven days later, all mice were challenged with $1\times10^6$ live wild-type cells subcutaneously in the neck. Tumor onset in the wild-type set was on post-challenge days 11 (2 mice), 12, and 15 (2 mice). Onset in the C3ba' set was on days 12, 15, 29, 38, and 39. The results revealed a survival period in the wild-type set of mice up to days 17, 19 (2 mice), 20, and 22; and a considerably longer survival period in the C3ba'-treated mice, i.e., up to days 19, 22, 37, 54, and 61.

EXAMPLE 6

In another experiment, the therapeutic efficacy of C3ba'-transfected CMS-5 cells was evaluated. Balb/c mice were challenged subcutaneously in the neck with $5\times10^5$ wild-type CMS-5 cells. Six days later, 5 mice were vaccinated subcutaneously in the abdomen with $1\times10^6$ wild-type CMS-5 cells, 5 with $1\times10^6$ C3ba'-transfected cells, 5 with a mixture of $5\times10^5$ wild-type and $5\times10^5$ GM-CSF-transduced cells (Dranoff et al, op. cit.), and 10 with a mixture or $5\times10$ C3ba'-transfected and $5\times10^5$ GM-CSF-transduced cells. All vaccinating cells were irradiated. The wild-type group developed tumors on days 11, 14 (3 mice), and 15, and survived until days 26, 39 (3 mice), and 43. Three C3ba' mice developed tumors on day 1, and survived until days 19 and 26 (2 mice). A fourth mouse however, developed a small tumor an day 16 that never progressed significantly, and this mouse did not require sacrifice even through day 60, after which the experiment was terminated. The fifth mouse had not developed a tumor when the experiment was terminated. All 5 of the wild-type/GM-CSF mice developed tumors on day 11. Two of these survived to day 19, and 3 to day 26. The C3ba'/GM-CSF mice developed tumors on days 11 (5 mice), 12 (2 mice), 15 (2 mice), and 43. They survived to days 26 (5 mice), 39 (2 mice), and 48 (1 mouse), with 2 mice's tumors never progressing significantly. The latter two did not require sacrifice through at least day 60.

EXAMPLE 7

In another experiment, C3ba'-transfected CMS-5 cells were studied as a preventive vaccine in the context of a large difference between number of vaccinating cells and number of challenging cells. Balb/c mice were vaccinated subcutaneously in the abdomen with $2 \times 10^5$ irradiated wild-type (5 mice) or C3ba'-transfected (10 mice) cells, or were not vaccinated (5 mice). Seven days later all mice were challenged subcutaneously in the neck with $2 \times 10^7$ live wild-type CMS-5 cells. All mice in the unvaccinated and wild-type sets developed tumors on day 9 and survived to day 15. In the C3ba' set, one mouse had not developed a tumor through at least day 60, while 8 mice developed tumors on day 9 and 1 on day 17. The mice that developed tumors survived until days 15 (4 mice), 17 (2 mice), 24 (2 mice), and 33.

EXAMPLE 8

In another experiment, B16 cells transduced with the mouse mannose binding protein A gene were studied as a preventive vaccine. C57BL/6 mice were vaccinated subcutaneously in the abdomen with $5 \times 10^5$ irradiated wild-type B16 cells (5 mice) or $5 \times 10^5$ irradiated MBP-transduced cells. Seven days later, these mice, as well as 5 unvaccinated mice, were challenged subcutaneously in the neck with $1 \times 10^6$ live wild-type B16 cells. The unvaccinated set developed tumors on days 9 (4 mice) and 12, and survived to days 13, 16 (3 mice), and 18. Tumors appeared in the wild-type set on days 9, 10, 12 (2 mice), and 13, with all surviving to day 18. Tumor onset in the MBP set was on days 10 (2 mice), 13 (3 mice), 16 (2 mice), 18, 21, and 28, with survival to days 17, 18 (4 mice), 24 (2 mice), 28 (2 mice), and 40.

Preparation of Engineered Opsonins

EXAMPLE 9

In one example, the alpha' chain of the C3b fragment of complement C3 is amplified by PCR (denaturation 60 sec/94° C., annealing 60 sec/57° C., extension 2.5 min/72° C.) from mouse liver cDNA using an upstream primer corresponding to nucleotides 2304–2324 of Genbank K02782 plus a 5' "ATG" and a downstream primer complementary to nt 5027–5045 of K02782, which omits the native stop codon. The GPI modification signal sequence of human CD16B is cloned by PCR (denaturation 60 sec/94° C., annealing 60 sec/57° C., extension 45 sec/72° C.) from human spleen cDNA using an upstream primer which corresponds to nucleotides 621–646 of Genbank XI 6863 and contains 12 bases at the 5' end that are complementary to the 5' end of the antisense strand of C3ba', and a downstream primer which complements nucleotides 715–735 of X16863 and incorporates a downstream extension with an appropriate restriction site. Both products are isolated by agarose gel electrophoresis (0.8% agarose for C3ba', 1.2% for CD16B GPI-ms), eluted from the excised agarose bands using glass beads, and quantitated by spectrophotometry. The two amplified sequences are fused to each other in-frame using the overlap PCR method. Briefly, equimolar amounts of the two fragments are used in a PCR reaction with excess amounts of upstream C3b primer and downstream CD16B primer (denaturation 60 sec/94° C., annealing 90 sec/50° C., extension 2.75 min/72° C.).

EXAMPLE 10

In another example, murine mannose binding protein A gene is amplified from mouse liver cDNA using an upstream primer corresponding to nt 124–148 of Genbank S42292, and a downstream primer complementary to nt 814–837 of S42292. The GPI modification signal sequence of human mesothelin is cloned by PCR (denaturation 60 sec/94° C., annealing 60 sec/57° C., extension 45 sec/72° C.) from human mesothelioma cDNA using an upstream primer which corresponds to nucleotides 1786–1805 of Genbank U40434 and contains 12 bases at the 5' end that are complementary to the 5' end of the antisense strand of MBP, and a downstream primer which complements nucleotides 1961–1986 of U40434 and incorporates a downstream extension with an appropriate restriction site. Both products are isolated by agarose gel electrophoresis (1% agarose for MBP, 1.2% for mesothelin GPI-ms), eluted from the excised agarose bands using glass beads, and quantitated by spectrophotometry. The two amplified sequences are fused to each other in-frame using the overlap PCR method. Briefly, equimolar amounts of the two fragments are used in a PCR reaction with excess amounts of upstream MBP primer and downstream mesothelin primer.

EXAMPLE 11

In another example, a transmembrane engineered opsonin comprising an APC-binding moiety of C3b is prepared. A portion of the C3b fragment of murine complement C3 is amplified by PCR from mouse liver cDNA using an upstream primer corresponding to nucleotides 2304–2324 of Genbank K02782 plus a 5' "ATG" and a downstream primer complementary to nt 2429–2453 of K02782. The transmembrane region of mouse IgG3 is amplified from mouse spleen cDNA using an upstream primer which corresponds to nucleotides 100–125 of Genbank V01526 and contains 12 bases at the 5' end that are complementary to the 5' end of the antisense strand of the C3b fragment, and a downstream primer which complements nucleotides 823–846 of V001526 and incorporates a downstream stop codon plus an extension with an appropriate restriction site. Both products are isolated by agarose gel electrophoresis (1.2% agarose for both), eluted from the excised agarose bands using glass beads, and quantitated by spectrophotometry. The two amplified sequences are fused to each other in-frame using the overlap PCR method. Briefly, equimolar amounts of the two fragments are used in a PCR reaction with excess amounts of upstream C3b primer and downstream IgG3 primer.

The above products can be cloned into suitable expression vectors, incorporating an upstream secretory signal if necessary, and expressed in the appropriate cells, e.g. insect cells.

Use of Engineered Opsonins to Prepare Opsonin-Enhanced Cells

EXAMPLE 12

Opsonin-enhanced cells can be prepared by introducing a nucleic acid encoding a engineered opsonin into the cells as described hereinabove. GPI-linked engineered opsonins can also be used to prepare opsonin-enhanced cells using the following procedure (McHugh et al, op. cit.). Cells are suspended in a suitable buffer, e.g. HBSS or phosphate-buffered saline, at a concentration on the order of $1 \times 10^5$ to $1 \times 10^8$ cells/ml. GPI-linked opsonin is added at on the order of 10–200 ug/ml, and the admixture is incubated at 37° C. for 2 h. Cells are washed in buffer three times before use.

Dosage, Mode of Administration and Pharmaceutical Formulations

The invention encompasses methods of modulating an immune response in a mammal to a selected antigen, the method comprising administering to a mammal a therapeutic amount of opsonin-enhanced cells, or administering a therapeutic amount of cells, for example, T lymphocytes, which have been sensitized ex vivo to the antigen by contacting isolated T lymphocytes to antigen presenting cells which have internalized opsonin-enhanced cells.

Cells described herein may be prepared as injectables, either as liquid solutions or suspensions; solid forms suitable for solution in or suspension in, liquid prior to infection can also be prepared. The preparation can also be emulsified, or the cells encapsulated in liposomes. The active immunogenic ingredients are often mixed with carriers which are pharmaceutically acceptable and compatible with the active ingredient. The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof In addition, if desired, the vaccine can contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydrox yphosphoryloxy)-ethylamine (COP) 19835A, referred to as MTP-PE), and RIBI, which contains three components extracted from bacteria, monophosporyl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as Iymphokines (e.g., IFN-, IL-2 and IL-12) or synthetic IFN-inducers such as poly I:C can be used in combination with adjuvants described herein.

Cells of the invention can be administered parenterally, by injection, for example, either subcutaneously or intramuscularly. Additional formulations which are suitable for other modes of administration include suppositories, and in some cases, oral formulations or formulations suitable for distribution as aerosols. In the case of the oral formulations, the manipulation of T-cell subsets employing adjuvants, antigen packaging, or the addition of individual cytokines to various formulation can result in improved oral vaccines with optimized immune responses. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25–70%.

The opsonin-enhanced cells of the invention can be formulated into the vaccine compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Any cellular component of such vaccine compositions can, in preparation for inclusion in such compositions, be subjected to treatments which involve attenuation or inactivation of the cells of the vaccine, including, for example, exposure to ionizing radiation, which can inhibit cell division, antiproliferative agents such as cyclophosphamide, cytochalasin D, or colchicine, or killing with or without fixation.

The opsonin-enhanced cells are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection desired. Suitable dosage ranges are of the order of several hundred micrograms active ingredient per vaccination with a preferred range from about 0.1 $\mu$g to 1000 $\mu$g, such as in the range from about 1 $\mu$g to 300$\mu$g, and preferably in the range from about 10 $\mu$g to 50 $\mu$g. Suitable regiments for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of opsonin-enhanced cells of this invention will depend, inter alia, upon the administration schedule, the unit dose of antigen administered, whether the cells are administered in combination with other therapeutic agents, the immune status and health of the recipient, and the therapeutic activity of the particular nucleic acid molecule or opsonin/antigen complex.

The cells can be given in a single dose schedule, or preferably in a multiple dose schedule. A multiple dose schedule is one in which a primary course of vaccination can include 1–10 separate doses, followed by other doses given at subsequent time intervals required to maintain and or reinforce the immune response, for example, at 1–4 months for a second dose, and if needed, a subsequent dose(s) after several months. Periodic boosters at intervals of 1–5 years, usually 3 years, are desirable to maintain the desired levels of protective immunity. The course of the immunization can be followed by in vitro proliferation assays of peripheral blood lymphocytes (PBLs) co-cultured with ESAT6 or ST-CF, and by measuring the levels of IFN-released from the primed lymphocytes. The assays can be performed using conventional labels, such as radionucleotides, enzymes, fluorescent labels and the like. These techniques are known to one skilled in the art and can be found in U.S. Pat. Nos. 3,791,932, 4,174,384 and 3,949,064, which are hereby incorporated by reference.

Other Embodiments

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove, are hereby expressly incorporated herein by reference to the extent that they describe, set forth, provide a basis for or enable compositions and/or methods which may be important to the practice of one or more embodiments of the present inventions.

I claim:

1. A method of vaccinating a mammal to a selected antigen, the method comprising
   administering to the mammal a vaccine composition comprising an opsonin-enhanced cell comprising said selected antigen in an amount effective to vaccinate said mammal to said-selected antigen, with the proviso that said opsonin of said opsonin enhanced cell does not bind to a receptor for a fragment of C3.

2. A method of vaccinating a mammal to a selected antigen, the method comprising
   administering to the mammal a vaccine composition comprising an opsonin-enhanced cell comprising said selected antigen in an amount effective to vaccinate said mammal to said selected antigen, said opsonin comprising a ligand for CR1, CR3, or CR4 which is not C3d, C3dg, or C3bi.

3. A method of vaccinating a mammal to a selected antigen, the method comprising
   administering to the mammal a vaccine composition comprising an opsonin-enhanced cell in an amount effective to vaccinate said mammal to said selected antigen, wherein said opsonin-enhanced cell comprises said selected antigen and is admixed with an exogenous opsonin, with the proviso that said opsonin of said opsonin-enhanced cell does not bind to a receptor for a fragment of C3.

4. A method of vaccinating a mammal to a selected antigen, the method comprising
   administering to the mammal a vaccine composition comprising an opsonin-enhanced cell in an amount effective to vaccinate said mammal to said selected antigen, wherein said opsonin-enhanced cell comprises said selected antigen and is admixed with an exogenous opsonin, said opsonin comprising C3b, the α' chain of C3b, or a fragment of the α' chain of C3b comprising at least about 500 amino acids.

5. A method of vaccinating a mammal to a selected antigen, the method comprising
   administering to the mammal a vaccine composition comprising an opsonin-enhanced cell in an amount effective to vaccinate said mammal to said selected antigen, wherein said opsonin-enhanced cell comprises said selected antigen and is admixed with an exogenous engineered opsonin, said opsonin comprising a fragment of the α' chain of C3b comprising at least the 42 N-terminal amino acids.

6. A method of vaccinating a mammal to a selected antigen, the method comprising
   administering to the mammal a vaccine composition comprising an opsonin-enhanced cell comprising said selected antigen in an amount effective to vaccinate said mammal to said selected antigen, wherein said opsonin is one of mannose binding protein or the alpha' chain of C3b.

7. A method of vaccinating a mammal to a selected antigen, the method comprising
   administering to the mammal a vaccine composition comprising an opsonin-enhanced malignant tumor cell comprising said selected antigen in an amount effective to vaccinate said mammal to said selected antigen.

8. A method of vaccinating a mammal to a selected antigen, the method comprising
   administering to the mammal a vaccine composition comprising an opsonin-enhanced malignant tumor cell in an amount effective to vaccinate said mammal to said selected antigen, wherein said opsonin-enhanced malignant tumor cell comprises said selected antigen and is admixed with an exogenous opsonin.

9. A method of vaccinating a mammal to a selected antigen, the method comprising
   administering to the mammal a vaccine composition comprising an opsonin-enhanced malignant tumor cell in an amount effective to vaccinate said mammal to said selected antigen, wherein said opsonin-enhanced malignant tumor cell comprises said selected antigen and is admixed with an engineered opsonin.

10. A method of vaccinating a mammal to a selected antigen, the method comprising
    administering to the mammal a vaccine composition comprising an opsonin-enhanced malignant tumor cell in an amount effective to vaccinate said mammal to said selected antigen, wherein said opsonin is one of mannose binding protein or the alpha' chain of C3b.

11. A method of vaccinating a mammal to a selected antigen, the method comprising
    administering to the mammal a vaccine composition comprising an opsonin-enhanced cell comprising said selected antigen in an amount effective to vaccinate said mammal to said selected antigen, said opsonin comprising C3b, the α' chain of C3b, or a fragment of the α' chain of C3b comprising at least about 500 amino acids.

12. A method of vaccinating a mammal to a selected antigen, the method comprising
    administering to the mammal a vaccine composition comprising an opsonin-enhanced cell comprising said selected antigen in an amount effective to vaccinate said mammal to said selected antigen, said opsonin comprising a fragment of the α' chain of C3b comprising at least the 42 N-terminal amino acids.

13. A method of vaccinating a mammal to a selected antigen, the method comprising
    administering to the mammal a vaccine composition comprising an opsonin-enhanced cell comprising said selected antigen in an amount effective to vaccinate said mammal to said selected antigen, said opsonin comprising a fragment of C3 that is not one of C3d, C3dg, or C3bi.

14. A method of vaccinating a mammal to a selected antigen, the method comprising
    administering to the mammal a vaccine composition comprising an opsonin-enhanced cell comprising said selected antigen in an amount effective to vaccinate said mammal to said selected antigen, said opsonin comprising an antibody that binds to CR1, CR3, or CR4.

15. A method of vaccinating a mammal to a selected antigen, the method comprising
    administering to the mammal a vaccine composition comprising an opsonin-enhanced cell in an amount effective to vaccinate said mammal to said selected antigen, wherein said opsonin-enhanced cell comprises said selected antigen and is admixed with an exogenous opsonin, said opsonin comprising a fragment of C3 that is not one of C3d, C3dg, or C3bi.

16. A method of vaccinating a mammal to a selected antigen, the method comprising administering to the mammal a vaccine composition comprising an opsonin-enhanced cell in an amount effective to vaccinate said mammal to said selected antigen, wherein said opsonin-enhanced cell comprises said selected antigen and is admixed with an exogenous opsonin, said opsonin comprising an antibody that binds to CR1, CR3, or CR4.

17. A method of vaccinating a mammal to a selected antigen, the method comprising administering to the mammal a vaccine composition comprising an opsonin-enhanced cell in an amount effective to vaccinate said mammal to said selected antigen, wherein said opsonin-enhanced cell comprises said selected antigen and is admixed with an exogenous opsonin, said opsonin comprising a ligand for CR1, CR3, or CR4 which is not C3d, C3dg, or C3bi.

18. A method of vaccinating a mammal to a selected antigen, the method comprising administering to the mammal a vaccine composition comprising an opsonin-enhanced cell in an amount effective to vaccinate said mammal to said selected antigen, wherein said opsonin-enhanced cell comprises said selected antigen and is admixed with an exogenous engineered opsonin.

19. The method of any one of claims 1–5 or 15–18 wherein said opsonin-enhanced cell is substantially unable to divide in vitro.

20. The method of any one of claims 1–5 wherein said vaccine composition is attenuated.

21. The method of any one of claims 1–5 or 6 wherein said antigen is a pathogenic cell.

22. The method of claim 1 or 2 or 11–14, wherein said opsonin-enhanced cell comprises said selected antigen and a nucleic acid encoding an opsonin and expresses said nucleic acid encoding said opsonin.

* * * * *